(12) United States Patent
Dirks

(10) Patent No.: US 10,785,929 B2
(45) Date of Patent: Sep. 29, 2020

(54) LINE DESIGN

(71) Applicant: RIJK ZWAAN ZAADTEELT EN ZAADHANDEL B.V., De Lier (NL)

(72) Inventor: Robert Hélène Ghislain Dirks, Oudenbosch (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 652 days.

(21) Appl. No.: 13/793,075

(22) Filed: Mar. 11, 2013

(65) Prior Publication Data
US 2014/0007286 A1 Jan. 2, 2014

(30) Foreign Application Priority Data

Jun. 29, 2012 (EP) .................................... 12174437

(51) Int. Cl.
*A01H 5/10* (2018.01)
*A01H 1/02* (2006.01)
*C12N 15/82* (2006.01)
*A01H 5/00* (2018.01)

(52) U.S. Cl.
CPC ................. *A01H 1/02* (2013.01); *A01H 5/00* (2013.01)

(58) Field of Classification Search
None
See application file for complete search history.

(56) References Cited

U.S. PATENT DOCUMENTS

| 2006/0179498 A1 | 8/2006 | Dirks et al. |
| 2008/0098496 A1 | 4/2008 | Van Dun et al. |
| 2011/0083202 A1 | 4/2011 | Chan et al. |
| 2012/0131688 A1 | 5/2012 | Dirks et al. |
| 2013/0298286 A1 | 11/2013 | Dirks et al. |
| 2014/0259208 A1 | 9/2014 | Dirks et al. |

FOREIGN PATENT DOCUMENTS

| WO | 03/017753 | 3/2006 |
| WO | 2006/094773 | 9/2006 |
| WO | 2011/044132 | 4/2011 |

OTHER PUBLICATIONS

Dirks et al 2009 (Plant Biotechnology Journal 7: p. 837-845).*
Wijnker and de Jong 2008 (Trends in Plants Science 13:12 p. 640-646).*
Tek et al 2015 (Turk J Agri For 39: p. 557-562).*
Knoll et al 2012 (The Plant Cell 24: p. 1448-1464).*
European Search Report dated Oct. 24, 2012, which issued during prosecution of European Application No. 12 17 4437.
Rob Dirks, et al. "Reverse Breeding: a novel breeding approach based on engineered meiosis" Plant Biotechnology Journal 7(9):837-845, Dec. 2009.
Erik Wijnker, et al. "Reverse breeding in *Arabidopsis thaliana* generates homozygous parental lines from a heterozygous plant" Nature Genetics, 44(4):467-470, Jan. 2012.

* cited by examiner

*Primary Examiner* — Matthew R Keogh
(74) *Attorney, Agent, or Firm* — Duane Morris LLP; Thomas J. Kowalski; Deborah L. Lu

(57) ABSTRACT

The present invention relates to a method for genetically modifying the genome of a hybrid plant by replacing one or more of its chromosomes or chromosome fragments with the corresponding chromosome or chromosome fragment of one or more donor parents. The invention uses the reverse breeding technique to construct a novel type of substitution and introgression libraries that can be used for accelerated breeding and hybrid correction. These libraries and their use are also part of this invention.

20 Claims, 9 Drawing Sheets

LINE DESIGN

RELATED APPLICATIONS AND INCORPORATION BY REFERENCE

This application claims priority to EP patent application No. 12174437.9 filed 29 Jun. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a method for genetically modifying the genome of a hybrid plant. It also relates to a library of chromosome substitution lines and/or introgression lines, and to the use of the libraries of chromosome and introgression lines thus obtained for accelerated plant breeding.

BACKGROUND OF THE INVENTION

Plant breeding aims at combining as many advantageous and attractive traits as possible in the same plant genome, with the goal of obtaining an elite plant line or variety. Thereby a plant breeder can take advantage of the genetic variation that occurs within the relevant crop species or within wild (uncultivated and undomesticated) relatives of the same species or genus.

He can also induce genetic variation in the genome of a plant species of interest by means of mutagenesis by chemical, physical or other means, and search for phenotypic variation that results from the induced genetic variation.

If he is willing and able to apply a transgenic approach, he can also choose to introduce one or more transgenes into the genome of a crop plant. These transgenes may correspond to genes, gene clusters or intergenic sequences that occur naturally in the same plant species or in a plant species that can be crossed therewith to give rise to fertile offspring. This is known as cisgenesis. Alternatively, they may correspond to synthetic genes or to DNA-fragments from organisms that cannot naturally cross with the plant species of interest, such as plants from another family, or organisms from different taxa, such as animals, fungi, viruses or bacteria. This is called transgenesis. These DNA-sequences are either introduced unchanged into the genome of the plant species of interest, or they are altered in some way, for example by recombinant technology with or without mutagenesis.

Transgenic technologies allow researchers to combine multiple DNA-constructs into the genome of the same plant, and thus to stack or pyramid different traits. This approach can ultimately result in the creation of plants that harbour a multitude of selected traits, by combinatorial stacking/pyramiding of transgenes encoding these traits. However, such transgenic approaches have a number of disadvantages.

The effect and/or functionality of a given transgene often depends strongly on the exact position in the plant genome into which it has been inserted. For any genetically modified lead to receive approval for commercial use and animal and/or human consumption, it needs to undergo very extensive regulatory procedures, which are immensely expensive and time-consuming. Authorization will often only be granted for a specific transgenic insertion event in a given genome. The stacking of multiple transgenes only makes this process more costly, tedious and complex. Also, in important parts of the worldwide food market, transgenic food is not allowed for human consumption.

A plant breeder who does not wish to produce or market transgenic plants will typically rely on classic breeding techniques in order to combine multiple traits of interest in a plant species. The breeding process encompasses a first step of mixing the genomes of two plants by means of crossing, which plants each comprise interesting genetic traits. Subsequently, the presence of the traits of interest needs to be traced among the progeny of the cross of these two plants, which is typically done on the basis of phenotypical analysis and/or genomic testing, such as DNA-marker analysis, Single Nucleotide Polymorphism (SNP) detection, DNA-sequencing, etc.

Because the entire genomes of the original plants have been mixed in the F1 product and recombined during meiosis, the various traits of the original parent plants will have been shuffled, and they segregate in the F2 progeny of the cross. The breeder then wishes to fix as many commercially attractive traits as possible in a single plant, while at the same time eliminating as many undesired traits as possible. His goal is the creation of a marketable, commercially attractive product that is competitive and successful in the market, due to e.g. a novel combination of various interesting phenotypical traits.

To achieve this goal, he needs to repeatedly cross the F1 plants derived from the cross of a parent plant and a donor plant back to the parent plant, and in every generation again select for individuals that harbour all of the desired traits, or as many as practically possible. This process is very time-consuming, as it usually takes at least six backcross generations and large progeny populations to obtain a line that is largely homozygous and resembling the parent plant, and into which one or more desired traits from the donor plant have been introgressed and fixed.

While some crops, such as lettuce, have a relatively short life cycle, other crops, such as carrot, require two years to produce seed. The generation of a new commercial line can thus easily take up to about 12 to about 20 years in such crops. Also, in the process of selection and subsequent back-crossing, nearly all of the genetic variation that was present in the genome of the donor plant or donor accession is lost, because the breeder specifically selects for one or a few traits of interest which he had initially identified, mostly phenotypically, in that donor accession. If the population size of each subsequent back-cross generation is limited (e.g. due to limited availability of growth space for the plants), the plant breeder will inevitably fail to notice and appreciate other potentially interesting traits that may be contributed by the genome of the donor accession. Classical breeding thus faces the problem of under-exploitation of the vast body of genetic variation that is present in e.g. wild accessions and uncultivated relatives of crop plants.

Citation or identification of any document in this application is not an admission that such document is available as prior art to the present invention.

SUMMARY OF THE INVENTION

It is an object of the present invention to provide an efficient method for producing non-transgenic plants with genomes into which selected genomic fragments, in particular full chromosomes or parts thereof from other genomes have been introduced. It is a further object of this invention to provide a fast, non-transgenic alternative to classical breeding, wherein hybrids may be efficiently constructed with genomic contributions from more than two parents, and wherein the breeding process may be perpetuated by means of a toolbox which represents as much genetic variation as desired from a given plant species. This toolbox may comprise collections of plant lines that each carry a different subset of chromosomes or chromosomal fragments, derived from one or more donor plants. In this application such collections are also referred to as libraries.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
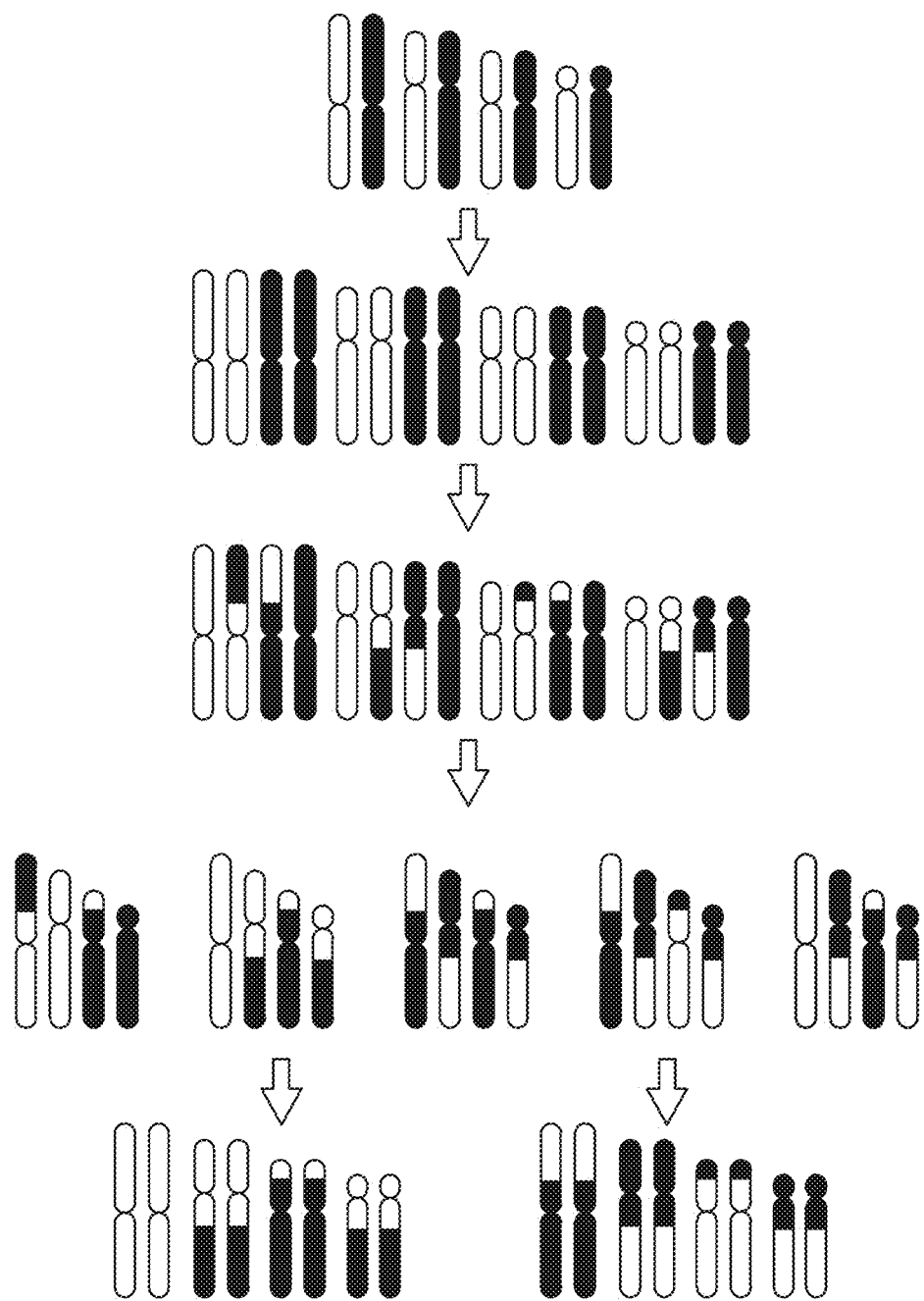
FIGS. 1A-B: Comparison of meiosis in the presence and absence of meiotic recombination, followed by DH production. Panel A illustrates the consecutive steps in the formation of DHs from an F1 hybrid plant, in the presence of meiotic recombination. After chromosome duplication (2n to 4n), genome-wide cross-over events occur randomly (meiotic recombination), resulting in the reshuffling of the chromosomes that were contributed to the hybrid genome by the two parental lines of the hybrid plant. During spore formation haploid chromosome sets (n) are formed, and when DHs are formed from these spores their genome is subsequently doubled. The end result is a population of RIL-like DHs (of which only two examples are shown here), in which a recombined genome is genetically fixed. Panel B, on the other hand, shows the consecutive steps in the formation of DHs from an F1 hybrid plant, in the absence of meiotic recombination. No reshuffling of the two parental genomes occurs, and the spores contain random and usually novel combinations of intact parental chromosomes. When DHs are formed from these spores their genome is doubled, and the end result is a population of homozygous chromosome substitution lines (or a homozygous chromosome substitution library). On the figure only two examples are shown. For simplicity this figure only shows four chromosomes, to illustrate the general principle.
Figure 1B:
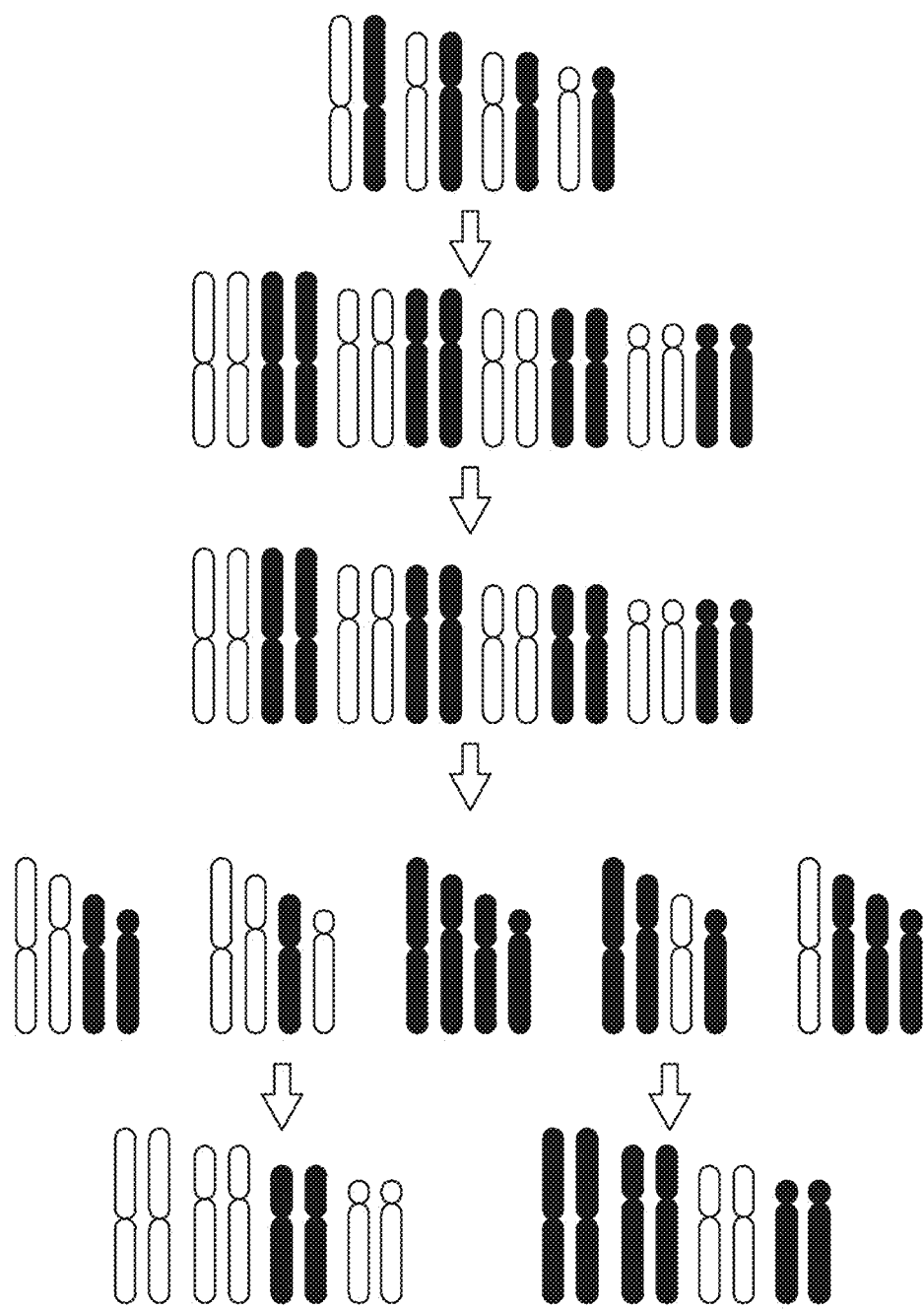

Reverse Breeding technology, as described and claimed in WO03/017753, allows the efficient production of homozygous plants from a heterozygous starting plant. This technology relies on the partial or complete suppression of meiotic recombination to allow the heterozygous starting plant to produce spores in which the chromosomes from the parents of that heterozygous starting plant have not been recombined. The parental chromosomes are thus transmitted to the spores and to the next generation in their entirety, without cross-overs with their sister chromatids. The difference between meiosis in the presence and absence of meiotic recombination is illustrated in FIG. 1.

From the spores obtained by the partial or complete suppression of meiotic recombination, haploid plants may be regenerated by means of e.g. androgenesis or gynogenesis protocols, or through the use of haploid inducer systems. The genome of these haploid plants is subsequently doubled. Genome doubling, which may occur spontaneously, or through the addition of mitosis-blocking chemicals such as colchicine, oryzalin or trifluralin, leads to the formation of doubled haploid plants (DH plants, DHs), which are able to produce seeds. In this manner the haploid lines are immortalized.

Figure 2A:
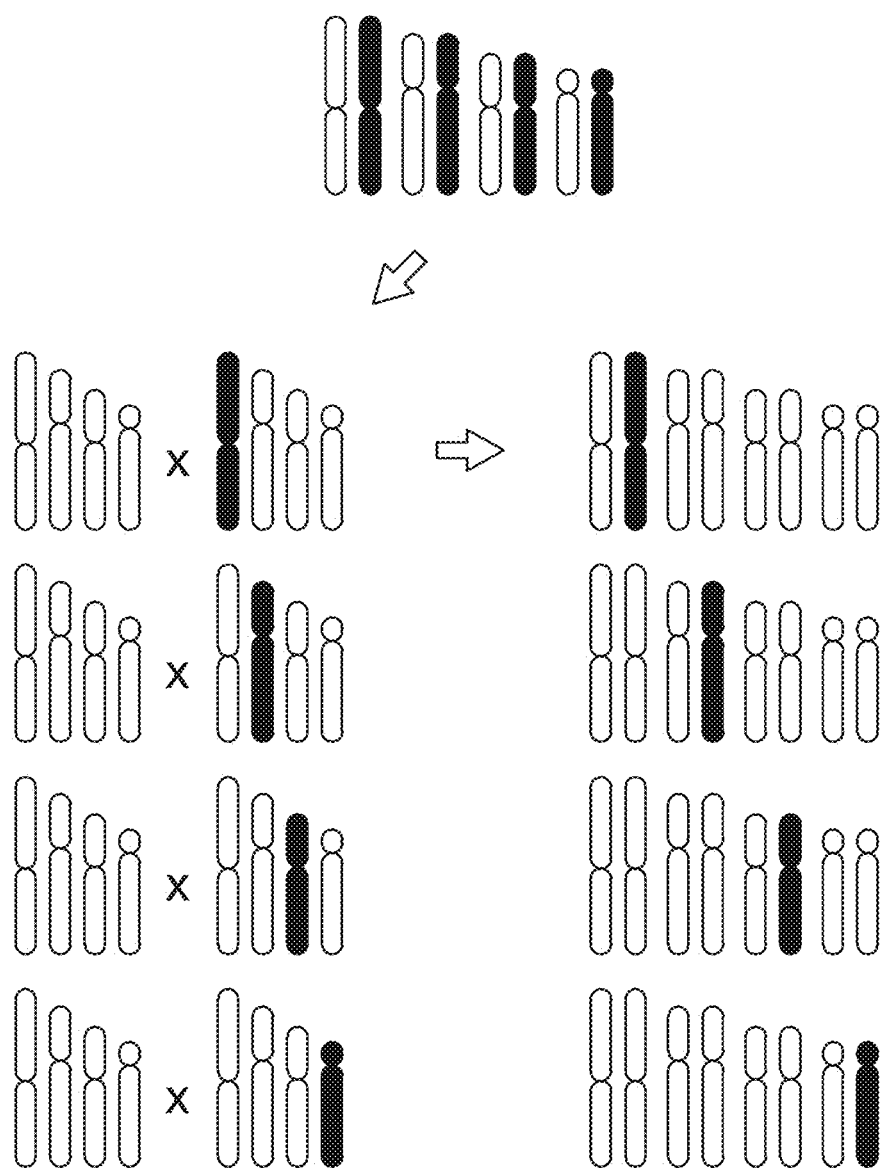
FIGS. 2A-B: Creation of substitution and introgression lines. Panel A shows the creation of four different chromosome substitution lines from an F1 hybrid plant (without showing the steps of FIG. 1; only the haploid chromosome set is shown here, while in fact DHs were created from the spores, whereby the chromosome set is doubled). When the DHs are backcrossed to one of the parental lines of the hybrid plant from which they were derived, this results in chromosome substitution lines which are heterozygous for one chromosome, but homozygous for the other chromosomes. Panel B illustrates how such a chromosome substitution line can be used to generate an introgression library for one chromosome. Importantly, meiotic recombination is allowed to proceed normally at this stage. The end result in this figure panel is a population of spores, wherein each individual spore contains the genome of the first parent of the hybrid plant, with one or more introgression fragments from the second parent of the hybrid plant in one of its chromosomes. For simplicity this figure only shows four chromosomes, to illustrate the general principle.

The DHs resulting from this method have a fully homozygous genome that consists of intact chromosomes that were inherited from the parents of the heterozygous starting plant, without the occurrence of recombination. There are various possible combinations of the original parental chromosomes, and the number of different DH lines depends entirely on the chromosome number of the plant species. Aneuploidy may occur at this stage, as the chromatids migrate randomly to one of the two cell poles during cytokinesis at the end of meiosis. When the resulting spore is euploid, i.e. contains the full complement of haploid chromosomes (n) typical for the species' genome, there are $2^n$ possible combinations of the parental chromatids. This is illustrated in FIG. 2A.

Either the DHs correspond exactly to one of the two parents of the heterozygous starting plant, or their genome consists of one or more chromosomes of the first parent combined with the remaining chromosome set of the second parent, to reach the full haploid chromosome number of the species. Such DHs are chromosome substitution lines, in which, when compared to one of the original parents of the heterozygous starting plant, at least one chromosome has been substituted with the intact corresponding chromosome from the other parent, without the occurrence of cross-over. A complete chromosome substitution library may comprise all chromosome substitution lines that may be obtained from a given heterozygous starting plant, and hence all possible combinations of chromosomes from both parental lines of that heterozygous plant.

A complete chromosome substitution library may e.g. be obtained directly from a given heterozygous starting plant by means of the partial or complete suppression of meiotic recombination (as in Reverse Breeding), or alternatively, especially when the chromosome number of the species is large, two rounds of partial or complete suppression of meiotic recombination (resembling two rounds of Reverse Breeding) may be required to obtain all possible chromosome substitution lines.

In the latter case, two different chromosome substitution lines, obtained through the partial or complete suppression of meiotic recombination, may be crossed, to give rise to a hybrid plant in which some of the chromosomes are present in a homozygous state, while other chromosomes are present in a heterozygous state. Application of the partial or complete suppression of meiotic recombination in this new hybrid plant results in the creation of additional chromosome substitution lines. This way of using meiotic recombination suppression in multiple steps reduces the number of heterozygous chromosomes and therefore increases very significantly the probability for obtaining desired unique karyotypes (specific combinations of the parents).

The inventors now contemplated that the technology of reverse breeding may be used to introduce interesting chromosomes or chromosomal fragments from one or more donor plants into an elite line or elite hybrid plant, by providing a method for genetically modifying the genome of a hybrid plant by replacing one or more of its chromosomes or chromosome fragments with the corresponding chromosome or chromosome fragment of one or more donor parents, which may comprise:
  a) crossing one of the parents of the hybrid plant with one of the donor parents, to obtain a first F1 population, allowing the F1 to produce spores while suppressing recombination, producing doubled haploids of the spores, to obtain a first population of chromosome substitution lines, b) optionally crossing the other parent of the hybrid plant with the same or another donor parent, to obtain a second F1 population, allowing the F1 to produce spores while suppressing recombination, producing doubled haploids of the spores, to obtain a second population of chromosome substitution lines, and either:

c1) producing a modified hybrid plant that has acquired one or more intact chromosomes of the donor parent(s), by selecting one individual of the first or the second population and crossing this individual with an individual of the other population or with a parent of the hybrid plant; or c2) producing a population of modified hybrids by:
  i. selecting one individual of the first or the second population and crossing this individual with the corresponding parent of the hybrid plant, and
  ii. allowing the progeny plant(s) resulting from this cross to produce spores, while allowing recombination to take place, to obtain a population of spores that have received one or more chromosome fragments of the donor parent, and making doubled haploids thereof, and
  iii. crossing the doubled haploid plants thus obtained with the other parent of the hybrid that is optionally modified, or with another homozygous line.

This invention essentially allows breeding per individual chromosome, while the rest of the plant's genome may remain unmodified. In this manner parental lines of elite hybrid varieties may be corrected in a very targeted manner, per individual chromosome, by replacing entire chromosomes or fragments thereof with corresponding chromosomes or chromosome fragments derived from one or more donor plants.

The method of the present invention, which is illustrated in FIG. 3, involves the creation of collections of chromosome substitution lines and/or collections of introgression lines, also called herein chromosome substitution libraries and introgression libraries, wherein parts of the genome of one or more donor accessions are fixed in the genome of elite parental lines from a breeding program. When these libraries are large enough, they may essentially harbour the entire genome of the one or more donor accessions, such that essentially all genetic variation present in the one or more donor accessions is fixed in the genome of elite parental lines from a breeding program.

Figure 4A:
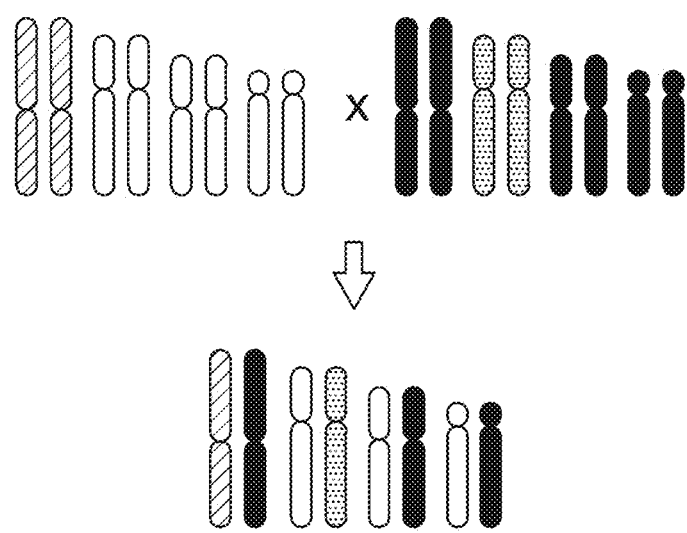
FIGS. 4A-C: Line Design at a higher level of complexity. Panel A shows (on the left) a homozygous chromosome substitution line from a first parental line, harboring one chromosome from a first donor plant, and (on the right) a homozygous chromosome substitution line from a second parental line, harboring one chromosome from a second donor plant). When these two DHs are crossed to each other, this results in an F1 which corresponds to a corrected version of the original F1 hybrid that would result from crossing the first parental line to the second parental line. The corrected hybrid harbors a chromosome copy contributed by the first donor plant for one of its chromosomes, and a chromosome copy contributed by the second donor plant for another of its chromosomes. In panel B the first and second parental lines have both acquired (through application of the method of the present invention) a chromosome from the second donor plant, and the result of crossing the two modified parental lines is a hybrid that is homozygous for the chromosome that had been contributed by the second donor plant. Panel C illustrates how this approach can be taken to an even higher level of complexity, wherein every chromosome of a hybrid has been contributed by a different plant. The hybrid of panel C essentially has genomic contributions from no less than six parents (two parental lines and four different donor plants), which is not feasible in a fast and efficient manner when using any previously known methodology. It is also possible to combine the scenario depicted in this Figure with the teachings of FIG. 2, to create introgression libraries with contributions from one or more donor plants. For simplicity this figure only shows four chromosomes, to illustrate the general principle.
Figure 4B:
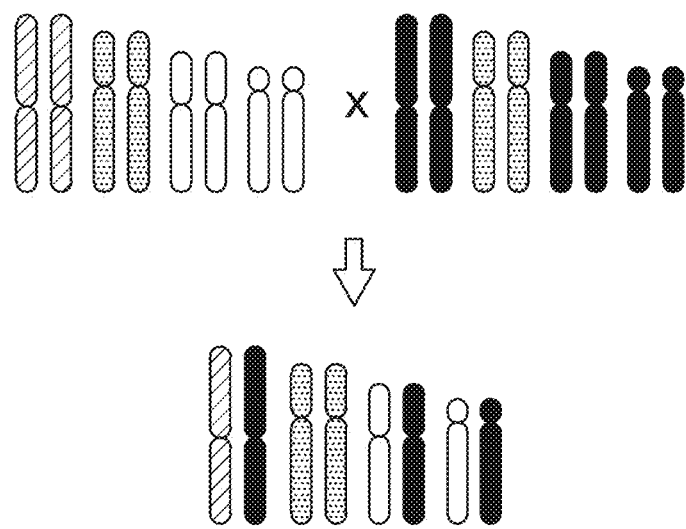
Figure 4C:
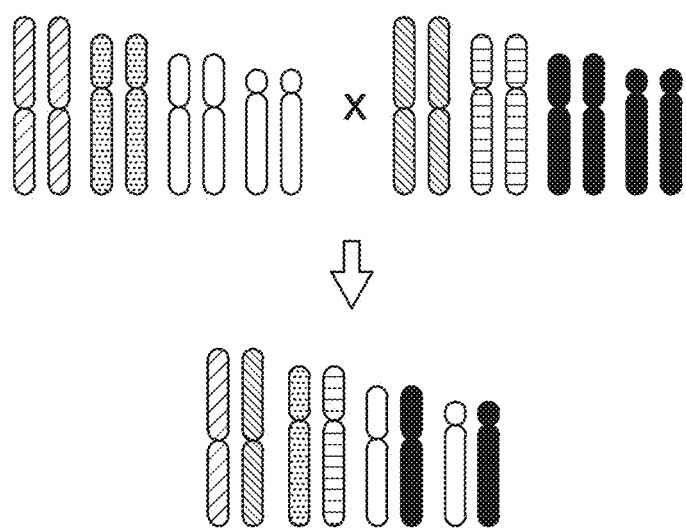

The method of this invention generally enables the creation of hybrids that are composed of selected genomic fragments which are derived from more than two parental lines, i.e. "multiparental hybrids", as for example illustrated in FIG. 4. Such "higher order hybrids" (ternary hybrids or tribrids, multibrids) provide maximal flexibility and selectivity to a plant breeder, and this method thus allows him to compose and design a plant genome by using large introgression libraries as a versatile toolbox, and as a virtually inexhaustible source of genetic variation in a given species or genus.

A donor plant either belongs to the same species as the parental lines, or to a species that may be successfully crossed with the parental lines to give viable and fertile offspring. The donor plant may either be a cultivated variety or a parental (inbred) line, or a wild accession, a genebank accession, or a transgenic plant, as is illustrated in the examples.

In angiosperms, a spore may be either a microspore or a megaspore. Both spore types are produced in the flowers, and microspores develop into the male gametophyte generation (pollen grain), whereas megaspores develop into the female gametophyte generation (embryo sac). Spores are typically the product of meiosis, and they are usually haploid, unless e.g. first division restitution or second division restitution occurs during meiosis, in which case the spores are diploid.

A substitution line (also referred to as "chromosome substitution line" in this application) is a line that harbours in its genome at least one chromosome from another line or plant. One or two copies of the original chromosome or chromosomes has/have been replaced by the corresponding copy or copies of that chromosome or chromosomes from another line or plant. A population of chromosome substitution lines which may comprise individual chromosome substitution lines that each harbour a different combination of chromosomes from two parental origins is termed a chromosome substitution library. A complete chromosome substitution library may comprise all possible combinations of parental chromosomes.

One may e.g. create chromosome substitution lines from two hybrids, which were obtained by crossing each of the two parental lines of an elite hybrid with a third plant, a "donor plant", which third plant harbours a trait of interest that was absent from the parental lines and their hybrid. If it is known on which chromosome of the donor plant the trait of interest resides and/or the presence of the trait may be identified by means of e.g. molecular markers or a detectable phenotype, it is possible to create specific chromosome substitution lines for each of the two parental lines, which may comprise in their homozygous genome all chromosomes of the parental line, but one chromosome of the donor plant.

From each chromosome substitution library a chromosome substitution line may then be selected, harbouring the donor plant's chromosome harbouring the desired trait. These chromosome substitution lines are identical to the parental lines, except for one chromosome which was contributed by the donor plant. The crossing of such two chromosome substitution lines will result in the exact reconstruction of the elite hybrid plant, with the exception of one chromosome pair. In contrast to the original elite hybrid plant the reconstructed or corrected hybrid plant is homozygous for the selected chromosome of the donor plant, and lacks the corresponding chromosomes from its two parental lines. This is illustrated in Example 1.

Alternatively, one may choose to replace a chromosome copy from only one of the parental lines in the elite hybrid with that of a donor plant. This strategy enables the targeted and controlled improvement of elite hybrid plants, by substituting one or more chromosomes with an improved version thereof, without the transgenic introduction of foreign DNA. This is illustrated in Example 3.

This approach may be taken to a higher level of complexity, by creating chromosome substitution lines between the individual parents of an elite hybrid and two different donor lines. In this manner, it is possible to substitute multiple chromosomes of the elite hybrid plant with chromosomes from different origins, and hence to bring sets of chromosomes together that may never occur in nature.

Through application of the current invention it is possible to create multiple chromosome substitution libraries in parallel, and to subsequently combine the individual chromosome substitution lines of different libraries with each other, to compose or design new genetic combinations. One may thus choose which chromosomes from the different genetic backgrounds are combined together in a chromosome set, in order to make up the complete chromosome set that constitutes the full genome of the species.

In the post-genomics era, it is becoming increasingly feasible to locate and positively identify the genomic variation that underlies agronomically important traits. Quantitative Trait Loci (QTL) mapping, marker development and genome sequencing in combination with association studies allow researchers to determine on which chromosome the genomic information leading to a particular phenotypic trait is encoded, and to narrow down this localization to a specific chromosome arm, to a chromosomal region, and ultimately to single loci and/or, in the case of SNPs, single nucleotides.

It is therefore also possible to refine the approach outlined above to the subchromosomal level, and to specifically create plant lines and hybrids that contain one or more selected introgression fragments from one or more donor plants in their genome, without any other genomic contribution from the donor plant(s). The advantages of this approach are enormous, as one may efficiently introduce genomic fragments harbouring desired genetic material into elite hybrid plants, without the complication of segregation of the traits that were already present in that elite hybrid, which is what would inevitably occur when the hybrid were to be crossed with the donor plant in order to introduce the desired genetic material from the donor plant by classical breeding, during which the parental genomes are typically mixed and recombined entirely.

In order to introduce chromosomal fragments from a specific chromosome of a donor plant into the hybrid of two parental lines, according to the present invention, one may first create a chromosome substitution line of one of the said parental lines, in which one of the chromosomes has been replaced by that of the donor plant. When this homozygous (Doubled Haploid) chromosome substitution line is subsequently backcrossed to the parental line from which it was derived, the resulting F1 plant is homozygous for all chromosomes, except for the chromosome that had been contributed by the donor plant. For the latter chromosome the F1 plant is heterozygous, harbouring in its genome one copy derived from the parental line and one copy derived from the donor plant.

Figure 2B:
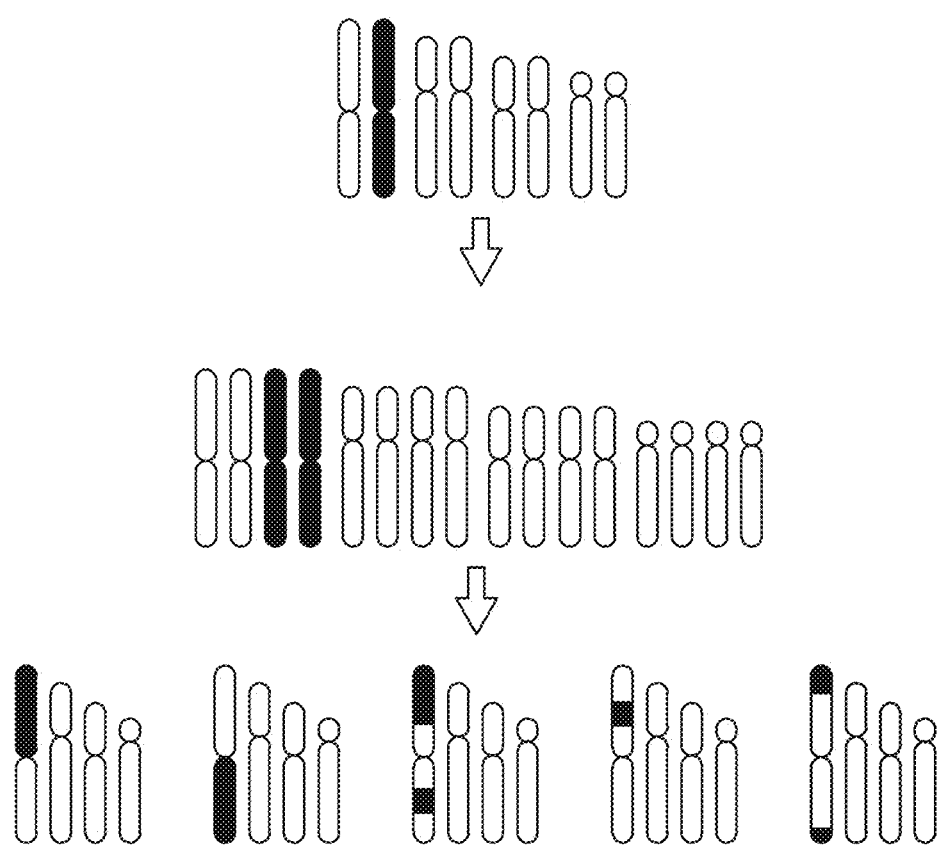
Figure 3A:
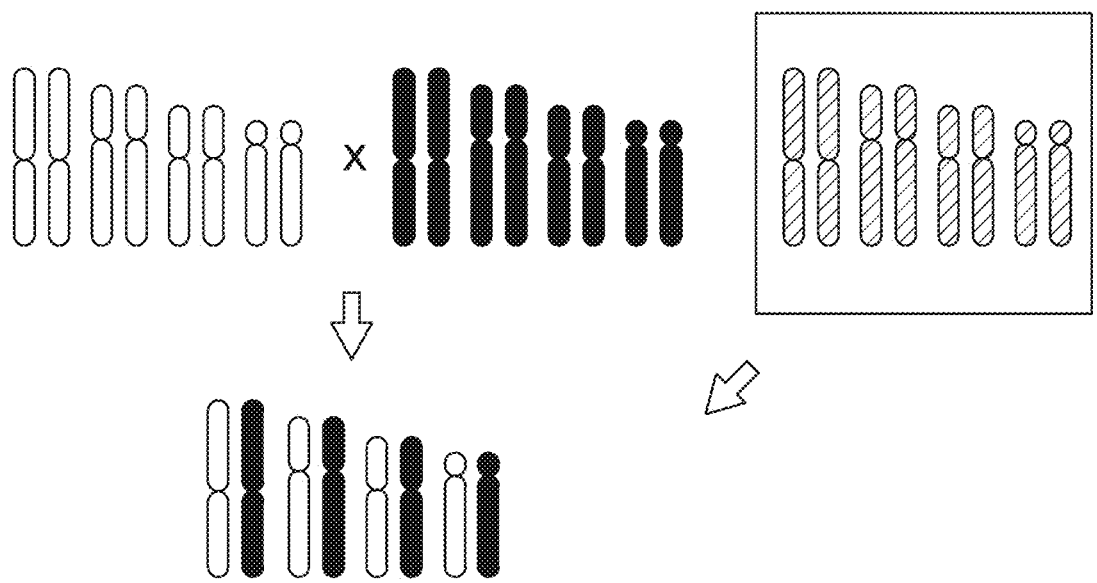
FIGS. 3A-F: Line Design. Panel A illustrates the plants that are essentially used in the method of the invention: two parental lines of a hybrid, and a third line (depicted in a frame) which is defined in this application as a donor plant, donor accession or donor parent. Panel B shows how one of the parental lines is crossed to the donor plant, giving rise to an F1 hybrid plant. In panel C this F1 hybrid plant is used for the creation of homozygous chromosome substitution lines, through the creation of DHs from the spores formed by this F1 hybrid in the absence of meiotic recombination, as illustrated in detail in FIGS. 1 and 2. In panel D one of the homozygous chromosome substitution lines, which corresponds to a "corrected" version of the first parental line of panel A, is crossed to the second parental line of panel A. The F1 of this cross corresponds to a corrected version of the hybrid plant of panel A. For one of its chromosomes one copy has been contributed by the donor plant, instead of by the first parental line. Panel E shows an alternative approach, wherein the procedure illustrated in panels B and C has (in parallel) also been performed on the second parental line of panel A. This resulted in the creation of chromosome substitution lines for both parental lines and (in this case) the same donor plant. In panel E, two homozygous chromosome substitution lines from different substitution libraries are crossed to each other, to give rise to a corrected version of the hybrid plant of panel A. For one of its chromosomes both copies have been contributed by the donor plant, instead of by the first and second parental line. Many alternatives are possible, e.g. wherein more than one donor plant is used, and/or wherein the two parental lines of panel A are "corrected" at different chromosomes (panel F), etc. If the chromosome substitution line of panel D is crossed to the first parental line of panel A (instead of to the second parental line), the situation of FIG. 2B is achieved: a "corrected" version of the first parental line, wherein one of the copies of one of the chromosomes has been replaced by a chromosome copy contributed by the donor plant. The procedure of FIG. 2B can then also be applied in this case: when at this stage meiotic recombination is allowed to proceed in an unsuppressed manner, this will lead to the creation of an introgression library. The individual DHs of this library may then possess one or more fragments of the corresponding chromosome of the donor plant. For simplicity this figure only shows four chromosomes, to illustrate the general principle.
Figure 3B:
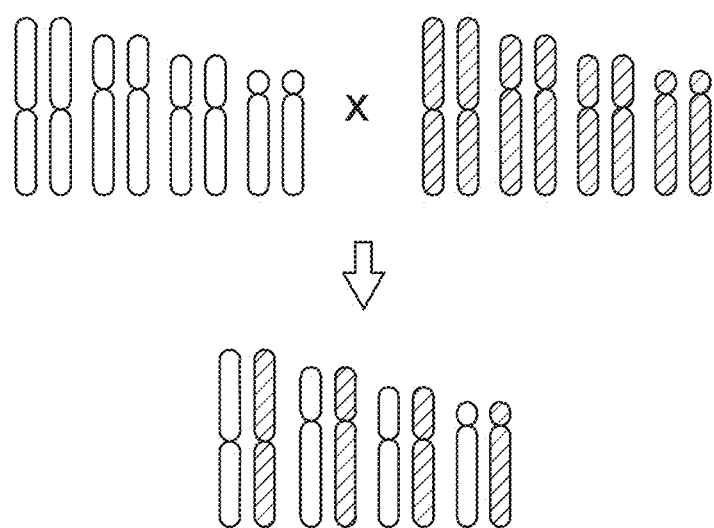
Figure 3C:
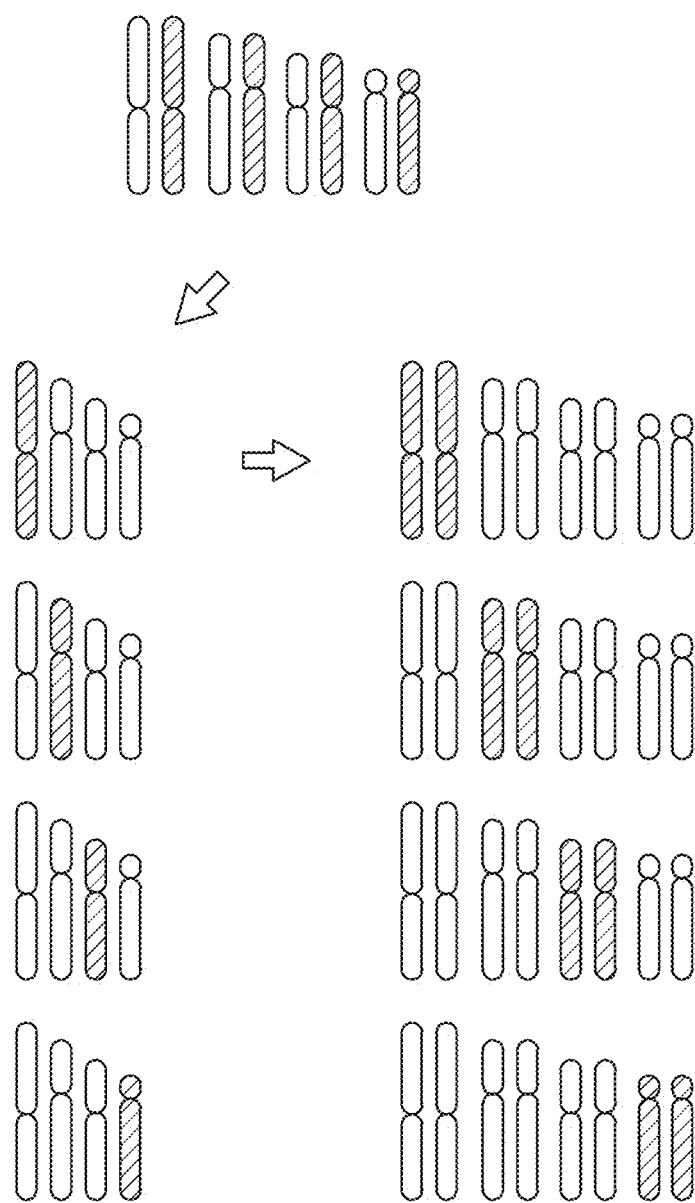
Figure 3D:
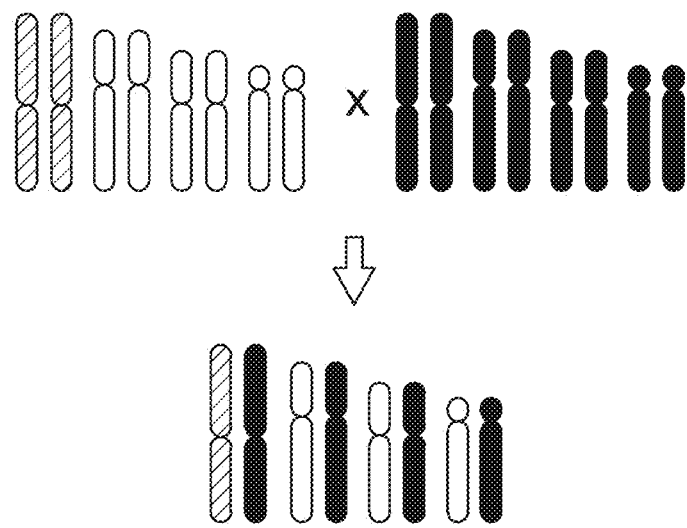
Figure 3E:
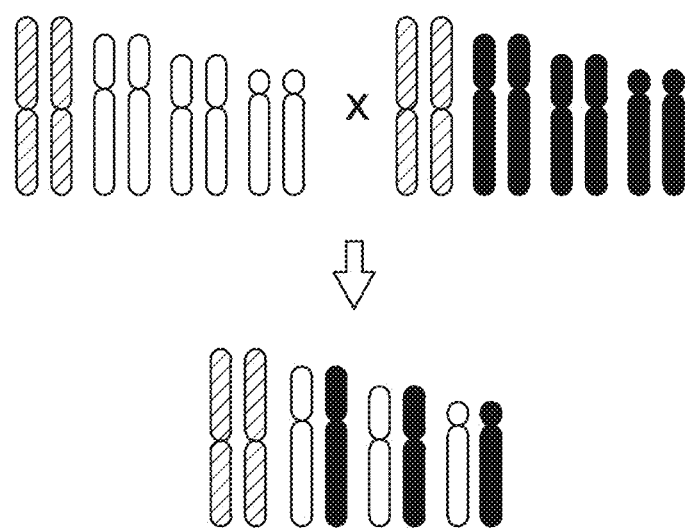
Figure 3F:
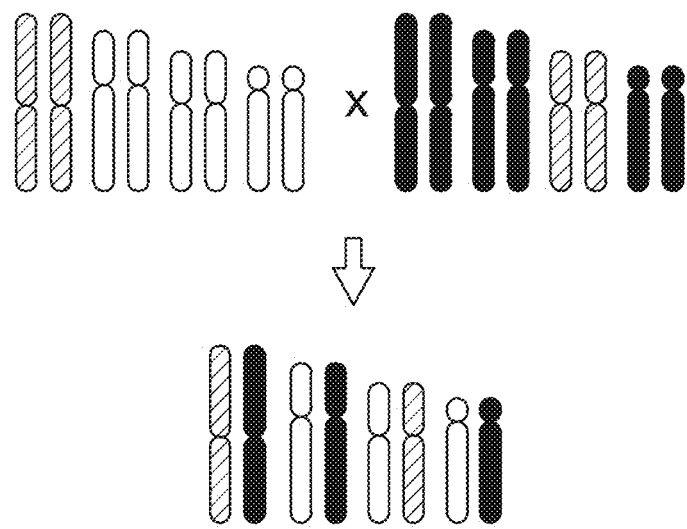

When this F1 plant is then allowed to produce spores without suppression of chromosome recombination during meiosis, and a DH population is created from these spores, this DH population will constitute a homozygous introgression library. Random recombination between the non-sister chromatids will occur for the one chromosome that was present in a heterozygous state, while recombination has no detectable effect on the other chromosomes, which are all present in a homozygous state. This is illustrated in FIG. 2B.

Because meiotic recombination occurs randomly during formation of the spores, and one or more recombination events may occur in each spore, a nearly infinite number of different DHs can be generated in this manner. These individual DHs will differ from each other and from the original parental line in the degree of introgression of the one chromosome from the donor plant into the parental line's genome.

This introgression may consist of a single chromosome fragment of the donor plant, or of multiple chromosome fragments of the donor plant, depending on the number of cross-over events that had occurred during the meiosis that gave rise to each individual spore. The size of the introgressed fragments may differ greatly, and it may range from very small fragments when two cross-over events occurred in close vicinity of each other, up to the entire chromosome when no cross-over had occurred. This approach also allows the mapping of cis-epistatic interactions within a chromosome.

An introgression line thus may comprise one or more chromosomal fragments from a donor plant, in the genomic context of another plant. A population of introgression lines which may comprise individual introgression lines that each harbour a different set of introgression fragments from a donor plant is termed an introgression library. The larger the population size is, the more complete an introgression library becomes, but in theory there is a nearly infinite number of introgression lines possible for any given chromosome. In the context of the present invention, introgression libraries are made per individual chromosome, and not randomly genome-wide. This is an important difference with introgression libraries as known in classical plant breeding. The introgression library of the invention thus preferably may comprise lines in which only one of the chromosomes has obtained one or more introgression fragments of the donor. A complete introgression library may comprise a set of introgression lines for each chromosome. Within each set all the other chromosomes remain constant and variation occurs only in the one chromosome belonging to the set.

This method allows the creation of plant genomes that are nearly identical to the genome of a parental line, but into which a specific chromosomal fragment from a donor plant has been introduced, in a fast, efficient and non-transgenic manner. By using molecular markers, genome sequencing and/or phenotypic analysis, it is possible to identify individual plants in such a homozygous introgression library, whose genome may comprise a chromosome fragment from the donor plant which harbours a trait of interest. Thus, a desired trait may specifically be introduced into the genome of a parental line or an elite hybrid plant, without the need for a transgenic approach or time-consuming and repetitive back-crossing. The genome of the parental line or hybrid plant is essentially "corrected", by replacing part of the genome with a corresponding part from another plant, while keeping the rest of the genome unchanged. This approach is illustrated in Examples 4, 5 and 7.

The present invention provides a method for genetically modifying the genome of a hybrid plant by replacing one or more of its chromosomes or chromosome fragments with the corresponding chromosome or chromosome fragment of one or more donor parents, which may comprise:

a) crossing one of the parents of the hybrid plant with one of the donor parents, to obtain a first F1 population, allowing the F1 to produce spores while suppressing recombination, producing doubled haploids of the spores, to obtain a first population of chromosome substitution lines, b) optionally crossing the other parent of the hybrid plant with the same or another donor parent, to obtain a second F1 population, allowing the F1 to produce spores while suppressing recombination, producing doubled haploids of the spores, to obtain a second population of chromosome substitution lines, and c) producing a modified hybrid plant that has acquired one or more intact chromosomes of the donor parent(s), by selecting one individual of the first or the second population and crossing this individual with an individual of the other population or with a parent of the hybrid plant.

The present invention also provides a method for genetically modifying the genome of a hybrid plant by replacing one or more of its chromosomes or chromosome fragments with the corresponding chromosome or chromosome fragment of one or more donor parents, which may comprise:
  a) crossing one of the parents of the hybrid plant with one of the donor parents, to obtain a first F1 population, allowing the F1 to produce spores while suppressing recombination, producing doubled haploids of the spores, to obtain a first population of chromosome substitution lines,
  b) crossing the other parent of the hybrid plant with the same or another donor parent, to obtain a second F1 population, allowing the F1 to produce spores while suppressing recombination, producing doubled haploids of the spores, to obtain a second population of chromosome substitution lines, and
  c) producing a modified hybrid plant that has acquired one or more intact chromosomes of the donor parent(s), by selecting one individual of the first or the second population and crossing this individual with an individual of the other population or with a parent of the hybrid plant.

In a further embodiment, the present invention provides a method for genetically modifying the genome of a hybrid plant by replacing one or more of its chromosomes or chromosome fragments with the corresponding chromosome or chromosome fragment of one or more donor parents, which may comprise:
  a) crossing one of the parents of the hybrid plant with one of the donor parents, to obtain a first F1 population, allowing the F1 to produce spores while suppressing recombination, producing doubled haploids of the spores, to obtain a first population of chromosome substitution lines,
  b) optionally crossing the other parent of the hybrid plant with the same or another donor parent, to obtain a second F1 population, allowing the F1 to produce spores while suppressing recombination, producing doubled haploids of the spores, to obtain a second population of chromosome substitution lines, and
  c) producing a population of modified hybrids by:
    i. selecting one individual of the first or the second population and crossing this individual with the corresponding parent of the hybrid plant, and
    ii. allowing the progeny plant(s) resulting from this cross to produce spores, while allowing recombination to take place, to obtain a population of spores that have received one or more chromosome fragments of the donor parent, and making doubled haploids thereof, and
    iii. crossing the doubled haploid plants thus obtained with the other parent of the hybrid, or with another homozygous line.

In yet another embodiment, the present invention provides a method for genetically modifying the genome of a hybrid plant by replacing one or more of its chromosomes or chromosome fragments with the corresponding chromosome or chromosome fragment of one or more donor parents, which may comprise:
  a) crossing one of the parents of the hybrid plant with one of the donor parents, to obtain a first F1 population, allowing the F1 to produce spores while suppressing recombination, producing doubled haploids of the spores, to obtain a first population of chromosome substitution lines,
  b) crossing the other parent of the hybrid plant with the same or another donor parent, to obtain a second F1 population, allowing the F1 to produce spores while suppressing recombination, producing doubled haploids of the spores, to obtain a second population of chromosome substitution lines, and
  c) producing a population of modified hybrids by:
    i. selecting one individual of the first or the second population and crossing this individual with the corresponding parent of the hybrid plant, and
    ii. allowing the progeny plant(s) resulting from this cross to produce spores, while allowing recombination to take place, to obtain a population of spores that have received one or more chromosome fragments of the donor parent, and making doubled haploids thereof, and
    iii. crossing the doubled haploid plants thus obtained with the other parent of the hybrid, or with another homozygous line.

The present invention also relates to a method for genetically modifying the genome of a hybrid plant by replacing one or more of its chromosomes or chromosome fragments with the corresponding chromosome or chromosome fragment of one or more donor parents, which may comprise:
  a) crossing one of the parents of the hybrid plant with one of the donor parents, to obtain a first F1 population, allowing the F1 to produce spores while suppressing recombination, producing doubled haploids of the spores, to obtain a first population of chromosome substitution lines,
  b) crossing the other parent of the hybrid plant with the same or another donor parent, to obtain a second F1 population, allowing the F1 to produce spores while suppressing recombination, producing doubled haploids of the spores, to obtain a second population of chromosome substitution lines, and
  c) producing a population of modified hybrids by:
    i. selecting one individual of the first or the second population and crossing this individual with the corresponding parent of the hybrid plant, and
    ii. allowing the progeny plant(s) resulting from this cross to produce spores, while allowing recombination to take place, to obtain a population of spores that have received one or more chromosome fragments of the donor parent, and making doubled haploids thereof, and
    iii. crossing the doubled haploid plants thus obtained with the other parent of the hybrid that is modified according to step b), or with another homozygous line.

Selecting one individual of the first or the second population may be done in any manner known to the skilled person. For example, the individual may be selected on the basis of phenotypical characteristics, and/or on the basis of genomic testing, such as by DNA-marker analysis, Single Nucleotide Polymorphism (SNP) detection, DNA-sequencing, etc.

Suppression of chromosome recombination may be achieved by interfering with one or more target genes involved in recombination. In one embodiment, the one or more target genes are involved in double strand breaks, such as SPO11, MER1, MER2, MRE2, MEI4, REC102, REC104, REC114, MEK1/MRE4, RED1, HOP1, RAD50, MRE11, XRS2, or their functional homologues.

The one or more target genes may also be involved in chromosome pairing and/or strand exchange, such as RHD54/TID1, DMC1, SAE3, RED1, HOP1, HOP2, REC8, MER1, MRE2, ZIP1, ZIP2, MEI5, RAD51, RAD52, RAD54, RAD55, RAD57, RPA, SMC3, SCC1, MSH2, MSH3, MSH6, PMS1, SOLODANCERS, HIM6, CHK2, or their functional homologues.

The one or more target genes may further be involved in the meiotic recombination process, such as SGS1, MSH4, MSH5, ZIP1 and ZIP2, or their functional homologues.

In another embodiment, the one or more target genes are selected from the group consisting of PRD1, PRD2, PRD3, PHS1, NBS1, COM1, MND1, MER3/RCK, ZIP3, ZIP4, PTD, SHOC1, ZYP1, MLH1, MLH3, or their functional homologues.

The interfering with the one or more target genes may consist of preventing transcription thereof. In a preferred embodiment, transcription is prevented by means of RNA oligonucleotides, DNA oligonucleotides or RNAi molecules directed against the target gene promoter. In another preferred embodiment, transcription is prevented by means of the expression of a negatively acting transcription factor acting on the target gene promoter.

The interfering with the one or more target genes may also consist of destabilizing the target gene mRNA or transcript, preferably by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides.

In yet another embodiment, the interfering with the one or more target genes consists of inhibiting the target gene expression product, preferably by means of the expression product(s) of one or more dominant negative nucleic acid constructs, or preferably by means of one or more chemical compounds.

In a further embodiment, the interfering with the one or more target genes consists of the introduction of one or more mutations into the target gene, leading to perturbation of its biological function, and the one or more mutations are preferably introduced randomly by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements, and/or the one or more mutations are introduced specifically by means of homologous recombination, oligo-nucleotide-based mutation induction, zinc-finger nucleases (ZFNs) or transcription activator-like effector nucleases (TALENs).

Doubled haploids may be produced of the spores by first creating haploid plants of the spores by means of androgenesis, such as microspore culture or anther culture, by gynogenesis, or by inducing the loss of maternal chromosomes from a zygote resulting from a fertilization event, and then doubling the genome of the haploid plants thus obtained.

Genome doubling may occur spontaneously, or it may be induced by the application of chemicals, such as colchicine, oryzalin or trifluralin. These chemicals disrupt spindle formation during mitosis, and are typically used for the blocking of mitosis.

The loss of maternal chromosomes from a zygote resulting from a fertilization event may be induced by using a haploid inducer line as the female in a cross. Haploid inducer systems have been described in various plant species. In one embodiment, the female is a plant of a different species. In interspecific crosses loss of the genome of one of the parents has often been observed, such as in the cross between wheat and pearl millet, between barley and *Hordeum bulbosum*, and between tobacco (*Nicotiana tabacum*) and *Nicotiana africana*.

The female plant may also be a transgenic plant that may comprise a heterologous transgene expression cassette, the expression cassette which may comprise a promoter operably linked to a polynucleotide encoding a recombinantly altered CENH3, CENPC, MIS12, NDC80 or NUF2 polypeptide, and having a corresponding inactivated endogenous CENH3, CENPC, MIS12, NDC80 or NUF2 gene. This embodiment has been first described in *Arabidopsis thaliana* (Maruthachalam Ravi & Simon W. L. Chan; *Haploid plants produced by centromere-mediated genome elimination;* Nature 464 (2010), 615-619; US-2011/0083202; WO2011/044132), and it is broadly applicable in plants.

Allowing recombination to take place may be achieved by no longer interfering with one or more target genes involved in recombination. When suppression of recombination had been achieved by means of a transgene, allowing recombination to take place is achieved by removing from the genome the transgene by which recombination may be suppressed, or by selecting for the absence of this transgene in the genome. When suppression of recombination had been achieved by means of one or more chemicals, allowing recombination to take place is achieved by not applying the one or more chemicals by which recombination may be suppressed.

In one embodiment, recombination is allowed to take place at an above-average frequency. In practice, however, the occurrence of multiple cross-over events in close vicinity of each other is naturally suppressed, such that introgression fragments are usually not very small. This phenomenon is known as chromosomal interference or cross-over interference.

Cross-over events may occur randomly along the length of a chromosome during meiotic recombination, and multiple cross-over events may occur in the same chromosome during the same meiosis. However, interference is known to occur between independent cross-over events, such that two recombination events usually do not occur in close vicinity of each other. During classical plant breeding this results in the carry-over of potentially large genomic fragments that are undesired and that may comprise genes with a negative effect, because these are genetically and physically linked to a desired trait for which the breeder selects, after crossing a cultivated line with for example a wild species.

Often these genomic fragments are difficult to remove when one wishes to retain the trait of interest, because it would require the occurrence of two cross-over events in the vicinity of the desired trait, which only very rarely happens. This problem is known as "linkage drag".

It is however possible to further increase the number of possible cross-over events during meiosis by increasing the recombination frequency. This may for instance be achieved by introducing a mutation in one or more genes that naturally suppress chromosome interference, such as FANCM, or by suppressing the expression of these genes, as illustrated in Example 8. This will result in an even larger possible number of different homozygous introgression lines, because it allows the occurrence of cross-over events in close vicinity of each other, and increase the overall number of cross-over events along a chromosome. This has the clear advantage that the introgressed fragments may be limited to only one or a few genes, and hence linkage drag can effectively be prevented. This further increases the efficiency of the method of the current invention.

In one embodiment, the interfering with the one or more genes that naturally suppress chromosome interference may consist of preventing transcription thereof. In a preferred embodiment, transcription is prevented by means of RNA oligonucleotides, DNA oligonucleotides or RNAi molecules directed against the gene promoter. In another preferred embodiment, transcription is prevented by means of the expression of a negatively acting transcription factor acting on the target gene promoter.

In another embodiment, the interfering with the one or more genes that naturally suppress chromosome interference consists of destabilizing the target gene mRNA or transcript, preferably by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides. In yet another embodiment, the interfering with the one or more genes that naturally suppress chromosome interference consists of inhibiting the target gene expression product, preferably by means of the expression product(s) of one or more dominant negative nucleic acid constructs, or preferably by means of one or more chemical compounds.

In another embodiment, the interfering with the one or more genes that naturally suppress chromosome interference consists of the introduction of one or more mutations into the gene, leading to perturbation of its biological function, and the one or more mutations are preferably introduced randomly by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements, and/or the one or more mutations are introduced specifically by means of homologous recombination, oligonucleotide-based mutation induction, zinc-finger nucleases (ZFNs) or transcription activator-like effector nucleases (TALENs).

This invention also relates to a library of substitution lines, which is obtainable by the method of the invention. Preferably, in such library in each of the substitution lines one chromosome is derived from the donor plant and the other chromosomes are derived from the parental line of the hybrid.

The invention furthermore relates to a library of introgression lines, which is obtainable by the method of the invention. Preferably, such library may comprise one or more sets of introgression lines wherein in each set of introgression lines one chromosome may comprise one or more introgression fragments derived from the donor plant and the other chromosomes are derived from a parental line of the hybrid. The library may comprise preferably a set of introgression lines for each chromosome. Preferably, each set varies in only one chromosome. This variation may be either by having replaced one or both copies of the original chromosome by a chromosome of the donor or having replaced one or more chromosome fragments on one or both copies of the original chromosomes. By combining the sets for each chromosome of a crop species a complete library may be construed that contains many possible variants. Since each line preferably only varies in one chromosome it is possible to effectively select only those lines for crossing that carry the desired chromosomes or chromosome fragments. Thus, repeated backcrossing to remove undesired chromosomes or chromosome fragments of the donor is no longer necessary. The lines in the libraries are preferably homozygous.

The invention thus further relates to use of such a library for accelerated plant breeding or hybrid correction. Accelerated plant breeding may comprise selection of one or more lines from the library that may comprise the desired donor chromosome or a chromosome carrying the desired donor-derived introgression fragment and crossing the selected lines with another plant, for example a parental line of the hybrid. Hybrid correction may comprise selection of a line that may comprise the desired donor chromosome or a chromosome carrying the desired donor-derived introgression fragment and crossing the selected lines with the other parent of the original hybrid. In one embodiment the other parent of the corrected hybrid is also selected from the substitution or introgression library.

The method outlined above enables a researcher or plant breeder to "correct" parental lines and the hybrid plants derived thereof in a very targeted and efficient manner, without necessarily rendering the resulting plants transgenic, and without requiring many generations of back-crossing. What is needed, is a preferably large homozygous introgression library, consisting of plants which each contain one or more random introgression fragments of different sizes, which are derived from one or more donor plants, and a means of reversibly achieving the partial or complete suppression of meiotic recombination, and of subsequently allowing meiotic recombination to proceed normally again.

Using the method of the invention, it is possible to create parental lines into whose genome a chromosome or chromosomal fragment from a donor plant has been specifically introgressed, without mixing and reshuffling the entire genomes of the parental lines and the donor plant. Plant breeding thus occurs per individual chromosome, while the other chromosomes of the plant remain intact, homozygous and thus unchanged. Chromosomes or chromosome fragments may be specifically exchanged, corrected and replaced, and undesired genetic features may be removed from a plant genome in a targeted manner.

The resulting "corrected" parental lines, produced in parallel with the method of the invention, may subsequently be crossed with each other, to give rise to hybrid plants whose genome may comprise the different introgression fragments which their parental lines had received from one or more donor plants.

It is hereby e.g. possible that one of the parental lines had received an introgression fragment from a donor plant on one of its chromosomes, while the other parental line had received an introgression fragment from the same or another donor plant on another chromosome. Crossing of these two parental lines would then result in a hybrid progeny plant with "corrections" on two chromosomes (either of the entire chromosomes, or of specific chromosomal fragments). This is e.g. illustrated in Example 4.

Alternatively, it is possible to again partially or completely suppress meiotic recombination during the formation of the spores of the F1 hybrid, in order to create DHs which are homozygous for the introgressed fragments. In this case the introgression fragment(s) are thus genetically fixed.

On an even higher level of complexity, it is also possible to continue this process by introgressing additional chromosome fragments from the same donor plant and/or from one or more different donor plants into the parental lines. This way, one may effectively "design" a plant genome, by introgressing selected chromosome fragments from different germplasm into elite parental lines, without mixing the entire genomes and thereby losing the combination of all other desired traits and genomic features that were already present in the parental lines. This method allows the efficient pyramiding of traits in plant genomes, without the need for repetitive back-crossing to fix the traits, as is the case in classical plant breeding, and without rendering the end products transgenic, as is the case when applying transgene technology.

In addition, when applying the method of the present invention the traits derived from the one or more donor accessions are introduced into the parental lines' genome in precisely the same genomic context and location as where they occurred in the donor plant(s). This is in contrast with transgene technology, wherein the integration site of the transgene is typically random and cannot be chosen. Such random insertion may lead to e.g. the disruption of endogenous genes in the parental line's genome and hence to additional undesired and unpredictable phenotypical effects, and generally the random nature of transgene insertion is a serious drawback of the transgene technology. When applying the method of the present invention, the chromosome fragments of the one or more donor plants essentially replace the corresponding chromosome fragments in the parental line(s), such that the genomic context is conserved.

In (homozygous) chromosome substitution libraries and (homozygous) introgression libraries the genetic variation from any number of donor lines may be fixed and adequately maintained for future use, in the genomic context of a parental line that is known to be suitable for the production of elite hybrids. This approach thus solves an important problem that exists in classical breeding, namely the fact that most of the natural variation that resides in the genome of donor plants (such as wild accessions) remains underexploited, unnoticed and unappreciated during the breeding process, because the breeder necessarily focuses his attention on predetermined traits of interest, and other genetic variation that is not closely genetically or physically linked to those predetermined traits is lost during the breeding process.

This is especially a problem for genetic variation that only results in a detectable phenotype when it is present in a homozygous state (e.g. recessive mutations), and that would be obscured by the presence of other, dominant allelic variants. The creation of homozygous chromosome substitution libraries and/or homozygous introgression libraries results in a large toolbox wherein such recessive traits may be assessed without any interference from dominant alleles from a different genetic background. If a specific homozygous introgression line exhibits a phenotype that was absent from the parental line from which it had been created, the genetic basis of that phenotype may be traced back to one of the introgression fragments that had been contributed to the plant's genome by the donor plant. Herein there is no risk that the trait will be lost or obscured again in the next generation, because the introgression line is a fully homozygous DH-line, which may produce seeds, and whose offspring through selfing will be essentially clones. This approach thus makes it possible to exploit the genome of a plant species in a much more efficient manner, and to optimally use the genetic variation that is present within a species or within a group of related species, to optimise the genetic features of plants of commercial interest that belong to that species or group of related species, such as vegetables, fruit trees, ornamental plants and field crops.

When applying the method of the present invention it is possible to e.g. identify a mutation or other genetic feature in the genome of an individual plant of a given species of interest, such as a parental line, or a wild uncultivated relative, or a mutagenised plant, or a transgenic plant, and to specifically and very efficiently introduce this mutation or genetic feature into an elite line of that species.

The present invention may be applied to all plant species that may be transformed and from which Doubled Haploid plants may be made. Crop species on which this invention may be practised include but are not limited to tobacco, poplar, maize, wheat, barley, rice, sorghum, sugar beet, oilseed rape, ryegrass, sunflower, cucumber, gherkin, corn salad, spinach, pepper, petunia, potato, eggplant, melon, watermelon, carrot, radish, lettuce, vegetable Brassica species (cabbage, cauliflower, broccoli, kohlrabi, Brussels sprouts), leek, bean, pea, endive, chicory, onion, strawberry, fennel, table beet, celery, celeriac, asparagus, sunflower, grape vine, cassava, cherry, apple, pear, peach, banana, tulip, petunia, rose, and *Chrysanthemum*.

Chromosome substitution lines (also termed "substitution lines") are lines that harbour in their genome at least one chromosome from another line or plant. One or two copies of the original chromosome or chromosomes from a first line or plant has/have been replaced (substituted) by the corresponding copy or copies of that chromosome or chromosomes from another line or plant. The remaining chromosomes are identical to those that were originally present in the first line or plant.

In the context of the present invention, a library of substitution lines (also termed "a library of chromosome substitution lines" or "a chromosome substitution library") is intended to mean a population of chromosome substitution lines which may comprise individual chromosome substitution lines that each harbour a different combination of intact chromosomes from two different parental origins. A complete chromosome substitution library may comprise all possible combinations of parental chromosomes from two different parental origins.

Introgression lines are lines or plants that comprise one or more chromosomal fragments from a donor line or plant, in the genomic context of another line or plant. A first line or plant can become an introgression line when its genome is mixed with the genome of a donor line or plant, and one or more chromosomal fragments from that donor line or plant are introgressed into the genome of the first line or plant.

In the context of the present invention, a library of introgression lines (also termed "introgression library") is intended to mean a population of individual introgression lines or plants that each harbor a different set of introgression fragments from a donor line or plant. In the context of the present invention, introgression libraries are made per individual chromosome, and not randomly genome-wide. This is an important difference with introgression libraries as known in classical plant breeding. The introgression library of the invention thus preferably may comprise lines or plants in which only one of the chromosomes has obtained one or more introgression fragments of the donor. A complete introgression library may comprise a set of introgression lines or plants for each chromosome. Within each set all the other chromosomes remain constant and variation occurs only in the one chromosome belonging to the set.

A homozygous introgression library consists of lines which each contain one or more random introgression fragments of different sizes, preferably on a single chromosome, which are derived from one or more donor lines or plants, and in which all chromosomes are present in a fully homozygous state, such that all genetic information is genetically fixed.

In the context of the present invention, the term "hybrid correction" is intended to mean the replacement of at least one chromosome copy or chromosome fragment in a hybrid genome with the corresponding chromosome copy or chromosome fragment from one or more donor lines or plants, without disturbing or losing the specific combination of traits that is present in the rest of the hybrid genome. In this manner, all desirable traits that had already been combined in the hybrid genome (and that would segregate away from each other in the next generation if the hybrid were to be allowed to sexually cross with itself or with a donor plant) remain unchanged, while specific defects or undesirable or commercially inferior traits in the hybrid genome can be "corrected" by replacing them with an alternative (commercially superior) version, without necessarily rendering the end-product transgenic. "Hybrid correction" may for example result in the introduction of wildtype alleles to replace unwanted mutant alleles, in the introduction of superior mutant alleles to replace wildtype alleles, in the site-specific introduction or elimination of transgenes, etcetera. "Hybrid correction" may thus for example lead to the removal of linkage drag, to the introduction of specific mutations and/or transgenes into a hybrid genome, and generally to fine-tuning and further improvement of a hybrid genome, without taking the risk of—due to segregation—losing the combination of desired traits that was already present in that hybrid genome. The actual genomic corrections are preferably performed in the parental line(s) of a hybrid organism, such that the effects of the genomic correction may be perpetuated in homozygous organisms, to be conveniently used and exploited in future research and breeding activities. In practice, "hybrid correction" may for example comprise the selection of a line that may comprise a desired donor chromosome or a chromosome carrying a desired donor-derived introgression fragment from a substitution or introgression library that had been made from the first parent of a hybrid, and crossing the selected line with the second parent of the hybrid, or with another line selected from a substitution or introgression library that had been made from the second parent of the hybrid. For the creation of substitution or introgression libraries from the first and/or the second parent of the hybrid either the same donor line or plant can be used, or genetically different donor lines or plants.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Chromosome Replacement in an *Arabidopsis* Hybrid

A hybrid *Arabidopsis thaliana* plant was created, by crossing a first plant of the Col-0 accession (homozygous) with a second plant of the Ler accession (homozygous). This Col-0×Ler hybrid was genotyped with two differentiating SNP-markers for each of the five chromosomes, to confirm its genomic make-up. For each of the five chromosomes the contribution of both parental accessions could be detected.

In order to recreate this hybrid and therein replace the two copies of one particular chromosome in this hybrid background with those from a third accession (Cvi) (homozygous), the claimed invention was applied as follows. In the terminology of this application the Col-0 and Ler plants are parental lines, and the Cvi plant is a donor parent, see e.g. FIG. 3A.

In a first step, an RNAi-construct targeting the DMC1 gene of *Arabidopsis* (Wijnker et al, 2012; *Nature Genetics* 44: 467-470) was introduced into the genome of Col-0 and Ler plants, using Agrobacterium-mediated transformation (Clough & Bent, 1998; *Plant J* 16: 735-743). From each accession a T0 plant was selected that harboured the transgenic construct in a heterozygous single-copy state (hemizygous). Molecular analysis and DNA-sequencing revealed that the transgene was inserted in chromosome II in the selected Col-0 plant, and in chromosome IV in the selected Ler plant. The transgene acts in a dominant fashion at the sporophytic level, such that meiotic recombination is suppressed during spore-formation in plants that harbour at least one copy of the transgene.

Subsequently, two chromosome substitution libraries were created, respectively for the Col-0 and Ler accessions: in the genome of Col-0 and Ler plants, one or more chromosomes were replaced by the corresponding chromosome or chromosomes from the genome of the Cvi donor accession. This was achieved by first (in parallel) crossing the transgenic Col-0 T0 plant with a Cvi plant and crossing the transgenic Ler T0 plant with a Cvi plant, and allowing the resulting hybrids to form spores in the absence of meiotic recombination. For this purpose progeny plants were selected that harboured the RNAi-construct against DMC1 in their genome, i.e. plants that had inherited the Col-0 or Ler chromosome copy harbouring the transgene. Because the original transgenic Col-0 and Ler plants were hemizygous for the transgene, also Col-0×Cvi and Ler×Cvi progeny was obtained that lacked the transgene, but in this example only progeny plants were selected that possessed the transgene, in order to suppress meiotic recombination during spore formation.

The presence of the transgene suppressed meiotic recombination, such that the selected Col-0×Cvi and Ler×Cvi hybrid plants produced microspores in which the parental chromosomes had not recombined. Instead, the chromosomes of both parental lines had been passed on to the microspores in their entirety, in random combinations.

Haploids from each selected hybrid were generated by means of centromere-mediated genome elimination (Ravi and Chan, 2010; *Nature* 464, 615-619; US patent application 20110083202; WO2011044132), followed by genome doubling. Alternatively, also other methods for the regeneration of haploid plants from spores may be used, such as gynogenesis, or microspore or anther culture protocols.

By thus suppressing recombination during the formation of the microspores of the hybrid plants, two populations of DH plants were created. The genome of the individual DH plants of these populations consisted of combinations of—in one case—intact, unrecombined Col-0 and Cvi chromosomes, and of—in the other case—intact, unrecombined Ler and Cvi chromosomes. Only spores with a correct haploid chromosome number (n=5 for *Arabidopsis*) were selected, and aneuploid spores were excluded from the further steps of the experiment. It is possible to identify balanced spores, for example by means of flow cytometry, or morphologically by visually selecting spores having a size that corresponds to the normal spore size of the species, which is indicative of an equal distribution of all chromosomes during spore formation.

By means of molecular markers capable of differentiating between the different accessions of which each DH was composed, the genomic constitution of each of the DHs was examined, in order to identify the origin of each of the five chromosomes in every individual DH plant. Two DH plants were selected in this manner:

A first plant harbouring chromosome I of Cvi in combination with the remaining 4 chromosomes from Col-0;

A second plant harbouring chromosome I of Cvi in combination with the remaining 4 chromosomes from Ler.

These two selected plants were subsequently crossed with each other, giving rise to hybrid progeny plants which were heterozygous for chromosomes II, II, IV and V (i.e. harbouring for each of these four chromosomes one copy from Col-0 and one copy from Ler), but homozygous for chromosome I. The latter chromosome originated from the Cvi accession, as could be confirmed by means of molecular markers. These hybrid progeny plants also harboured two copies of the RNAi transgene (one on chromosome II of Col-0 and the other on chromosome IV from Ler; both transgenes were present in a heterozygous state in the hybrid). The outcome of this example corresponds to panel E of FIG. 3.

Example 2

Chromosome Replacement in an *Arabidopsis* Hybrid, with a Non-Transgenic End-Product In Example 1 the resulting hybrid progeny was transgenic in nature (resulting in a regulated GMO-status and additional phenotypic difficulties resulting from the presence of the RNAi construct targeting DMC1, which e.g. leads to partial sterility due to the occurrence of aneuploidy, caused by the suppression of meiotic recombination during spore formation).

In the current example this problem is overcome, by including additional experimental steps in the procedure, after selection of the following two DH plants:

A first plant harbouring chromosome I of Cvi in combination with the remaining 4 chromosomes from Col-0;

A second plant harbouring chromosome I of Cvi in combination with the remaining 4 chromosomes from Ler.

The first plant was (back)-crossed once to a wildtype, non-transgenic Col-0 plant, and the second plant was (back)-crossed once to a wildtype, non-transgenic Ler plant. Due to the dominant nature of the DMC1 RNAi construct, suppression of meiotic recombination occurred in the spores produced by the hybrid plants resulting from these backcrosses. DHs were produced from euploid (balanced) microspores produced by the F1 plants, and these DHs were screened with molecular markers, to identify the origin of each of their five homozygous chromosome pairs, as described in Example 1.

At this stage not only aneuploid individuals were excluded, but also individuals that harboured the RNAi-construct targeting DMC1. In the DH plants resulting from the Col-0×Cvi hybrid only those individuals that carried the wildtype copy of Col-0 chromosome II—lacking the transgene—were selected, in combination with the presence of chromosome I from Cvi, and a similar selection strategy was applied for chromosome IV in the DH plants resulting from the Ler×Cvi hybrid. This selection ensured that the selected DH plants were non-transgenic, and that meiotic recombination would proceed uninterruptedly during meiosis in these selected plants.

The result of this selection was a non-transgenic DH plant harbouring chromosome I of Cvi in combination with the remaining 4 chromosomes from Col-0, and a non-transgenic DH plant harbouring chromosome I of Cvi in combination with the remaining 4 chromosomes from Ler.

These two selected plants were subsequently crossed with each other, giving rise to hybrid progeny plants which were heterozygous for chromosomes II, III, IV and V (i.e. harbouring for each of these four chromosomes one copy from Col-0 and one copy from Ler), but homozygous for chromosome I. The latter chromosome originated from the Cvi accession, as could be confirmed by means of molecular markers.

This procedure thus allowed the fast and efficient replacement of chromosome I in a hybrid background, without affecting the integrity of the other chromosomes, and without rendering the resulting hybrid transgenic. It did not require multiple rounds of backcrossing, and each chromosome was transferred in its entirety, without recombination. This approach can e.g. be useful in cases wherein one or more undesired traits are present on one of the chromosomes of an otherwise suitable hybrid, and a superior chromosome has been identified in another plant, accession, or wild relative. This superior chromosome can then be used to replace both copies of that chromosome in the hybrid background, without changing the rest of its genetic make-up.

Example 3

Replacement of One Chromosome Copy in an *Arabidopsis* Hybrid

In the same experiment, a Col-0×Ler hybrid was created that contained within its genome only one copy of chromosome I from Cvi. This was achieved by selecting a DH plant originating from the chromosome substitution library of Col-0 (as described in Example 1), whose genome comprised chromosome I from Cvi and all other chromosomes from Col-0, and which (in contrast to the plant selected in Examples 1 and 2) lacked the DMC1 transgene on chromosome II.

This plant was subsequently crossed to a wildtype Ler plant, to give rise to hybrid progeny. These progeny plants were fully hybrid for chromosomes II, III, IV and V (i.e. their genome comprised one Col-0 copy of each of these chromosomes, in addition to one Ler copy of each of these chromosomes), but which contained one Ler copy of chromosome I and one Cvi copy of chromosome I, but no Col-0 copy of that chromosome. In this manner the Col-0×Ler hybrid had thus been "corrected", such that the Col-0 copy of chromosome I had been specifically replaced by a Cvi version of that chromosome, without affecting the rest of the genome of this hybrid. This example corresponds to panel D of FIG. 3.

One can imagine plenty of situations in which this would be an attractive strategy, for example when one copy of a particular chromosome in a hybrid background may comprise a dominant mutation that causes an undesired phenotype in an otherwise perfect hybrid. It could also be used to remove a transgene from a hybrid, by replacing the chromosome harbouring the transgene by another (non-transgenic) copy.

Example 4

Introgression of Chromosome Fragments into an *Arabidopsis* Hybrid

In the same experiment, a fourth approach was undertaken: the creation of an introgression library for chromosome I from Cvi in a Col-0 background, and for chromosome II from Cvi in a Ler background. The first step was the creation of a chromosome substitution library for Col-0×Cvi and for Ler×Cvi, as described in Example 1.

From among the Col-0×Cvi chromosome substitution library a non-transgenic DH plant (lacking the RNAi transgene) was selected whose genome consisted of chromosome I from Cvi and the other four chromosomes from Col-0 (this DH plant had already been selected in Example 3). From among the Ler×Cvi chromosome substitution library a non-transgenic DH plant (lacking the RNAi transgene) was selected whose genome consisted of chromosome II from Cvi and the other four chromosomes from Ler.

Subsequently, the selected plants were backcrossed to one of their parent accessions (namely to wildtype Col-0 in the former case and to wildtype Ler in the latter case), similar to the illustrations in FIG. 2. The non-transgenic F1 plants resulting from these back-crosses were:

In case of Col-0×Cvi: heterozygous for chromosome I (one copy from Col-0 and one from Cvi), and homozygous (Col-0) for chromosomes II, III, IV and V.
In case of Ler×Cvi: heterozygous for chromosome II (one copy from Ler and one from Cvi), and homozygous (Ler) for chromosomes I, III, IV and V.

These F1 plants were allowed to form spores, without interference with meiotic recombination, because the RNAi construct targeting DMC1 was not present in their genomes. During spore formation, cross-over events took place across the entire genome, but because four of the five chromosomes were present in a homozygous state, there was only a detectable effect of recombination on the one chromosome that was present in a heterozygous state: chromosome I in case of Col-0×Cvi, and chromosome II in case of Ler×Cvi.

For the one heterozygous chromosome, recombination took place randomly in each of the spores, such that the individual spores in the population of spores produced by the F1 plants differed from each other only in the composition of that one chromosome. In some cases no recombination took place, while in other cases one or multiple cross-over events occurred in that chromosome.

These spores were subsequently used for DH production, as described in Example 1. The resulting DHs were, as is typically the case for all DHs, fully homozygous, and their genome was fixed. These DHs were identical to each other for four of their five chromosomes, but differed in the degree of introgression of Cvi fragments into the remaining chromosome. The population of DHs resulting from this experiment represented an introgression library for one chromosome.

The larger this population is, the greater the variation of introgression segments is available for study and use in breeding. The individual DHs from this introgression library were examined in detail using molecular markers capable of distinguishing between the three parental *Arabidopsis* accessions. This analysis confirmed that individual plants could be identified in which recombination had occurred between chromosome I from Col-0 and Cvi (while chromosomes II, III, IV and V were entirely derived from Col-0), and that individual plants could be identified in which recombination had occurred between chromosome II from Ler and Cvi (while chromosomes I, III, IV and V were entirely derived from Ler).

This analysis thus demonstrated that chromosome I (in the former case) and chromosome II (in the latter case) harboured one or more fragments derived from the corresponding chromosome from Cvi, while the other chromosomes had remained unchanged during this procedure.

Selected DHs obtained in this manner were subsequently crossed to each other, and this resulted in the creation of Col-0×Ler hybrids with "corrected" chromosomes I and II. They were identical to the original Col-0×Ler hybrid, except for the replacement of specific chromosomal fragments on chromosomes I and II. These regions originated from Col-0 and Cvi and from Ler and Cvi, respectively, whereas the rest of the hybrid genome consisted of an equal contribution from Col-0 and Ler.

In practice, this method can be used to e.g. replace "suboptimal" chromosome fragments in the parental lines of an otherwise suitable hybrid, or to introduce chromosome fragments that can further improve the hybrid (e.g. fragments containing specific allelic variation, or a transgene).

A great advantage of this method is the speed with which it can be carried out, e.g. when compared to classical breeding. Importantly, when one would attempt to create introgression lines using classical breeding methods known in the prior art, this would initially lead to introgression events on all five chromosomes. It would then require at least six generations of backcrossing to the original parental line to "purify" the genome of as many undesired introgression fragments as possible, while every time selecting for the presence of the desired introgression fragments.

In this example, one would thus start by crossing a Col-0 plant with a Cvi plant, and allow the F1 progeny of this cross to produce spores in the presence of recombination, and to self-fertilise. In the F2 generation of the cross one would subsequently screen for individuals that harbour in their genome the desired introgression fragment derived from the Cvi genome, and backcross these individuals to Col-0. This routine would be repeated at least another five times, or until a genome-wide marker analysis would indicate that the genome of the selected plants was predominantly derived from Col-0, with only the desired introgression fragment(s) from Cvi being present in their genome. The same routine would need to be done in parallel for the Ler×Cvi combination. Ultimately, one would e.g. obtain a Col-0 plant with one or more specific introgression fragments derived from Cvi on one chromosome, and a Ler plant with one or more specific introgression fragments derived from Cvi, in this case on another chromosome. Finally, these two selected plants could then be crossed to each other, to obtain a Col-0×Ler F1 hybrid with specific contributions from Cvi in its genome.

When comparing the time required for this classical approach to the time required to achieve this result with the method of the present invention, it is clear that the latter is far more efficient and fast. The experiment outlined above (Example 4) requires the following steps:

the production of two chromosome substitution libraries in parallel, through transformation with a suitable transgenic construct for the suppression of meiotic recombination, crossing (one generation), and a DH-step;

the selection of suitable individuals from the substitution libraries, one backcross generation followed by a DH-step, and selection, and crossing of selected lines.

This process is thus much faster than an initial cross followed by six or more backcross generations, the selection of suitable lines and another cross to obtain a hybrid (in total at least eight generations from seed to seed), which would be required in the classical breeding approach.

Depending on the speed and efficiency of the available protocol for transformation and DH-production in a given species, the method of the invention can be very fast, as one does not always need to wait for seed production after crossing, but merely for the production of spores, which are to be used for DH-production. Especially when a very efficient DH-protocol is available (such as a haploid-inducer system), the method of the invention can be very fast.

Apart from the speed, another clear advantage of the method of the invention is the fact that the genomic contributions of the donor plant(s) can be fixed and perpetuated in homozygous form in chromosome substitution and/or introgression libraries, such that they remain available in a stable manner in the genomic background of the parent line(s), where they can be used for future screens and exploitation in breeding. It is also a significant improvement over the prior art that introgression libraries can be made per individual chromosome, which is impossible when using classical breeding methods.

Example 5

Specific Transfer of a Transgene in Maize, while Maintaining the Exact Insertion Position of the Trans Gene In this example a transgene is introduced into an elite maize line, without directly transforming it into that line. The transgene is first introduced into a maize line that is easily transformable, and the best of many independent transgenic events can be selected for transfer into an elite maize line. Hereby the exact genomic insertion position of the transgene is maintained.

Genetically modified maize plants of the A188 genotype were obtained by Agrobacterium-mediated transformation, using the protocol described by Ishida et al (*Nature Protocols* 2, 1614-1621; 2007). The transgene used in this experiment was a GFP marker (Green Fluorescent Protein) with a nuclear localisation signal, operably linked to a strong ubiquitin promoter. This construct enables high levels of GFP expression throughout transformed maize plants, which is easily detectable due to the accumulation of the fluorescent GFP protein in the nuclei of cells.

From among the transformed A188 maize plants obtained in this experiment an individual was chosen that contained a single copy of the transgene in its genome, on chromosome VIII. In a first step, this selected transgenic line was crossed to elite line B73, which contained in its genome an RNAi construct targeting the DMC1 gene (also on chromosome VIII, single copy insertion, hemizygous). The latter transgene acted in a dominant fashion, such that meiotic recombination during spore formation was suppressed in the resulting hybrid progeny.

From the F1 progeny plants of this cross microspores were collected, and these were used for DH production, with a method known to the person skilled in the art.

From among the resulting DH plants, which corresponded to chromosome substitution lines, an individual was selected that possessed all chromosomes from B73, except for chromosome VIII, which was derived from A188. This plant was back-crossed to a wildtype B73 plant lacking the RNAi construct targeting DMC1, to give rise to progeny plants that were heterozygous for chromosome VIII (one copy derived from B73 and the other from A188, harbouring the GFP-transgene), but that fully corresponded to wildtype B73 with respect to the other nine chromosomes (n=10 for maize).

In the absence of the RNAi construct targeting DMC1, meiotic recombination was allowed to occur during spore formation in these progeny plants. Their spores were used for the production of DH plants (as described above), and in these DHs all chromosomes except for chromosome VIII were exclusively derived from the B73 background, whereas chromosome VIII was essentially derived from B73, with random introgression fragments from the A188 line.

From among this DH population homozygous individuals could be selected which contained only a relatively small fragment of A188 DNA on chromosome VIII, while still possessing the GFP transgene (which could be easily detected with the help of molecular markers). In this manner the transgene was effectively transferred from an A188 maize plant to the B73 elite line, without the need for transforming B73 directly with this construct, and without mixing the B73 genome with that of A188. This would have necessitated multiple rounds of backcrossing to B73 to obtain progeny plants that would closely resemble B73 again.

This approach allowed the large-scale production of transgenic lines in the easily transformable A188 background, and the selection of the best transgenic insertion event, which was subsequently transferred into B73, which is far less amenable to transformation, at exactly the same genomic location as in A188.

It is clear that this method could also be used for other transgenes, for example transgenes conferring resistance to herbicides or herbivoric animals, conferring disease resistance or increased tolerance to adverse conditions, providing higher yield, etc.

Similarly, using this method it is also possible to remove transgenes from the genome of a transgenic plant, without affecting the composition of the rest of its genome. The chromosome region or the entire chromosome containing the transgene is thereby replaced by a corresponding wildtype fragment from another line. Very specifically one chromosome can be "corrected" independently from the rest of the genome, and this correction generally entails the replacement of a full chromosome or of a chromosomal fragment.

Example 6

Efficient Breeding for Heterosis in Maize

Heterotic effects can increase the yield of hybrids quite significantly. They encompass the phenotypic outperformance of both parental lines by the F1 hybrid plant that results from their cross. Even though the molecular or genetic nature of heterosis is still unknown, empirical studies have provided valuable information in crops. For example in maize, various heterotic groups have been identified on the basis of pedigree information or molecular marker analysis, such as SSR (Simple Sequence Repeat) or SNP (Single Nucleotide Polymorphism) markers. Examples of such heterotic groups are Flint, Lancaster, Stiff Stalk, and Iodent (Van Inghelandt et al, 2010; *Theor. Appl. Genet.* 120: 1289-1299), or Dent (*Zea mays* indentata), Flint (*Zea mays* indurata) and Sweet (*Zea mays* rugosa or *Zea mays* saccharata). Each heterotic group may comprise a number of inbred lines with a certain degree of genetic similarity to each other. In order to get heterotic effects in the next generation, one typically needs to cross inbred lines from different heterotic groups with each other.

Generally the creation of a new maize hybrid exhibiting heterosis may comprise the improvement of parental lines of two different heterotic groups, and the subsequent crossing of those parental lines to obtain F1 hybrid seed. The improvement of parental lines encompasses classical plant breeding and/or transgenesis or cisgenesis, and in each hybrid genome contributions from only two heterotic groups can be brought together.

When applying the method of the current invention, it is however possible to bring more than two heterotic groups together in a single hybrid. What is needed is information on the chromosome regions that contribute to the heterotic nature of a group, such that these regions from an inbred line from one heterotic group can be specifically transferred into the genome of an inbred line from another heterotic group. This is similar to the approach described in Example 5, using chromosome substitution and/or introgression libraries.

In this manner, an inbred line from a first heterotic group is specifically improved to also contain heterotic genomic regions from a second heterotic group. In a next step, this improved inbred line can be crossed to an inbred line from a third heterotic group, which can in itself also have been improved, using the method of the current invention, to contain genomic material from more than one heterotic group. The genetic basis for heterosis is thereby brought together in cis and/or trans, within the same chromosome set. The result of this approach is the creation of hybrid maize plants that harbour the genetic material of not two, but of three or even more heterotic groups at once. This offers powerful new possibilities for increasing, for example, hybrid yield in maize.

Example 7

Specific Transfer of a Virus Resistance into a Melon Hybrid

Cucurbit Yellow Stunting Disorder Virus (CYSDV) is a closterovirus that is transmitted by the whitefly *Bemisia tabaci*, and that affects cucurbit crops such as melon (*Cucumis melo*). A genetic trait conferring resistance to this virus had been identified in *Cucumis melo* accession TGR-1551 from Zimbabwe (López-Sesé and Gómez-Guillamón, 2000; *Hort. Sci.* 35: 110-113). This example explains how—by means of the present invention—this dominant monogenic resistance trait can be efficiently transferred to an elite melon hybrid variety, without the need for many backcross-generations.

In a first step, an RNAi-construct targeting the DMC1 gene of melon was introduced into the genome of the father line of an elite melon hybrid, using the improved transformation protocol for Cantaloupe melons developed by Guis et al, 2000 (*Sci. Hort.* 8: 91-99). A T0 melon plant was selected that harboured the transgenic construct in a heterozygous single-copy state (hemizygous). Complementary pairs of father and mother lines for the elite melon hybrid can e.g. be obtained by the skilled person through the application of Reverse Breeding, using an elite melon hybrid plant as heterozygous starting organism, as described and claimed in WO03/017753.

The transgenic father line was grown alongside melon accession TGR-1551, which harboured in its genome a genetic trait conferring resistance to CYSDV. Subsequently the transgenic melon plant was crossed to accession TGR-1551, and the resulting hybrid offspring plants—selected to harbour the RNAi construct against DMC1 in their genome—were allowed to form spores in the absence of meiotic recombination. The spores formed by these F1 plants comprised random combinations of the intact chromosomes of both parental lines, as meiotic recombination had not occurred during their formation.

Megaspores produced by the F1 plants were regenerated into doubled haploid (DH) plantlets by means of gynogenesis, as described by e.g. Malik et al, 2011 (*Hort. Sci.* 38: 27-34), and subsequent chromosome doubling (Lim & Earle, 2009; *Plant Cell, Tissue & Organ Culture* 98: 351-356).

The genome of the individual DH plants of the DH population obtained in this manner consisted of combinations of intact, unrecombined chromosomes from both parental lines. Only plantlets with a correct haploid chromosome number (n=12) were selected, and aneuploid individuals were excluded from the further steps of the experiment. DHs harbouring the chromosome copy with the RNAi construct were also excluded at this stage.

By means of molecular markers capable of distinguishing between each of the chromosomes of the two parental lines of which each DH's genome was composed, the genomic constitution of each of the DHs was examined, in order to identify the origin of each of the 12 chromosomes in every individual DH plant. DH plants were selected that harboured in their genome the chromosome from TGR-1551 on which the CYSDV resistance trait was located, which could be detected empirically by means of a resistance assay known to the skilled person, and which for the remaining eleven chromosomes exhibited a molecular marker pattern that was identical to that of the father line of the elite melon hybrid, and lacking the RNAi construct targeting DMC1. Such plants were fully homozygous chromosome substitution lines, in which one chromosome from TGR-1551 carrying the CYSDV resistance trait was combined with 11 chromosomes from the father line of the elite melon hybrid, to form a full genomic complement.

In principle, these selected lines, which showed resistance to CYSDV, as could be confirmed experimentally using resistance tests known to the skilled person, could already be used to construct a CYSDV-resistant hybrid, by crossing it with a suitable mother line. However, because one of the chromosomes of the "corrected" father lines was entirely derived from TGR-1551, this would only lead to an incomplete reconstruction of the elite melon hybrid variety. To overcome this problem and to be able to accomplish an almost perfect hybrid reconstruction, an introgression library was produced in the next step of the experiment, to limit the genomic contribution of the TGR-1551 line to a chromosomal fragment which may comprise the resistance trait.

For this purpose, the selected DH plants were subsequently backcrossed to the father line of the elite melon hybrid. Because the said father line was almost entirely homozygous (being a pure line), 11 of the 12 chromosomes were virtually present in a homozygous state in the F1 progeny resulting from this cross, because the DH plants were fully homozygous, and possessed 11 of the 12 chromosomes from the said father line. For the remaining chromosome one copy derived from line TGR-1551, harbouring the CYSDV resistance trait, and one copy derived from the said father line were present in the F1 progeny of this cross.

Meiotic recombination during spore formation in these F1 plants specifically resulted in random crossing-over events between the two copies of this chromosome. The F1 plants were allowed to form spores, and another DH population was created from the megaspores that were produced by these progeny plants, by means of gynogenesis. These DH plants effectively constituted a non-transgenic introgression library for the chromosome harbouring the CYSDV resistance trait from the TGR-1551 line, in the genetic background of the father line of the elite melon hybrid. The remaining 11 chromosomes remained largely unchanged, such that the only major difference between the individual DHs in this introgression library existed in the number, size and position of the introgression fragments of the chromosome copy derived from TGR-1551 into the chromosome copy derived from the father line of the elite melon hybrid.

By means of virus resistance tests and molecular markers a DH plant was identified that harboured in its genome a relatively small introgression fragment from TGR-1551, which may comprise the CYSDV resistance trait. This DH plant was subsequently confirmed to be CYSDV resistant. The selected DH line essentially corresponded to a corrected version of the father line of the elite melon hybrid, because a fragment of one of its chromosomes was specifically replaced with the corresponding fragment from another melon accession, and in this process a dominant resistance trait was introduced into its genome.

This "corrected" line was subsequently crossed to the mother line of the elite melon hybrid, and the (non-transgenic) F1 progeny of this cross had all the characteristic features of the elite melon hybrid variety, in addition to a CYSDV resistance.

Example 8

Efficient Pyramiding of Traits in *Arabidopsis* with Increased Recombination Frequency Genetic determinants have been discovered that are responsible for the "cross-over interference" phenomenon that underlies e.g. linkage-drag. One such factor is the FANCM gene, which has been shown to play a key role in the control of meiotic cross-over formation in *Arabidopsis thaliana* (Knoll et al, 2012; *Plant Cell* 24: 1448-1464; Crismani et 2012; *Science* 336: 1588-1590).

Suppression of FANCM expression and/or activity in plants abolishes the interference between individual crossover events, such that more recombination events can occur per chromosome or chromosome region during a single meiosis. The genetic map size of a plant species can thus greatly be increased by suppressing FANCM expression or by interfering with FANCM activity, and linkage-drag can thereby be removed in a convenient manner.

The invention is further described by the following numbered paragraphs:

1. Method for genetically modifying the genome of a hybrid plant by replacing one or more of its chromosomes or chromosome fragments with the corresponding chromosome or chromosome fragment of one or more donor parents, comprising:
    a) crossing one of the parents of the hybrid plant with one of the donor parents, to obtain a first F1 population, allowing the F1 to produce spores while suppressing recombination, producing doubled haploids of the spores, to obtain a first population of chromosome substitution lines,
    b) optionally crossing the other parent of the hybrid plant with the same or another donor parent, to obtain a second F1 population, allowing the F1 to produce spores while suppressing recombination, producing doubled haploids of the spores, to obtain a second population of chromosome substitution lines, and
    either:
    c1) producing a modified hybrid plant that has acquired one or more intact chromosomes of the donor parent(s), by selecting one individual of the first or the second population and crossing this individual with an individual of the other population or with a parent of the hybrid plant;
    or
    c2) producing a population of modified hybrids by:
        i. selecting one individual of the first or the second population and crossing this individual with the corresponding parent of the hybrid plant, and
        ii. allowing the progeny plant(s) resulting from this cross to produce spores, while allowing recombination to take place, to obtain a population of spores that have received one or more chromosome fragments of the donor parent, and making doubled haploids thereof, and
        iii. crossing the doubled haploid plants thus obtained with the other parent of the hybrid that is optionally modified, or with another homozygous line.

2. Method of paragraph 1, wherein allowing recombination to take place is achieved by removing from the genome the transgene by which recombination can be suppressed, or by not applying the one or more chemicals by which recombination can be suppressed.

3. Method of paragraph 1, wherein recombination is allowed to take place at an above-average frequency.

4. Method of paragraph 3, wherein the above-average frequency of recombination is achieved by interfering with one or more target genes involved in the suppression of recombination, such as FANCM.

5. Library of substitution lines, obtainable by the method of paragraph 1.

6. Library of paragraph 5, wherein in each of the substitution lines one chromosome is derived from the donor plant and the other chromosomes are derived from the parental line of the hybrid.

7. Library of introgression lines obtainable by the method of paragraph 1.

8. Library of paragraph 7, comprising one or more sets of introgression lines wherein in each set of introgression lines one chromosome comprises one or more introgression fragments derived from the donor plant and the other chromosomes are derived from a parental line of the hybrid.

9. Library of paragraph 7 or 8, comprising a set of introgression lines for each chromosome.

10. Use of a library of any one of the paragraphs 5-9 for accelerated plant breeding or hybrid correction.

11. Use of paragraph 10, wherein accelerated plant breeding comprises selection of one or more lines from the library that comprise the desired donor chromosome or a chromosome carrying the desired donor-derived introgression fragment and crossing the selected lines with another plant.

12. Use of paragraph 11, wherein the other plant is a parental line of the hybrid.

13. Use of paragraph 10, wherein hybrid correction comprises selection of a line that comprises the desired donor chromosome or a chromosome carrying the desired donor-derived introgression fragment and crossing the selected lines with the other parent of the hybrid.

14. Use of paragraph 10, wherein hybrid correction comprises selection of a line that comprises the desired donor chromosome or a chromosome carrying the desired donor-derived introgression fragment and crossing the selected lines with another line selected from the substitution or introgression library.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for producing a modified hybrid plant, said method comprising replacing a chromosome or chromosome fragment of a hybrid plant with the corresponding chromosome or chromosome fragment of a donor parent of the hybrid plant ("the replacement chromosome or chromosome fragment"), said replacing comprising:
   (a) crossing a first parent of the hybrid plant with the donor parent, to obtain a first F1 population,
   (b) allowing the first F1 population to produce spores while suppressing meiotic recombination,
   (c) producing doubled haploids of the spores of the first F1 population, to obtain a first population of chromosome substitution lines,
   (d) crossing a second parent of the hybrid plant with the donor parent of step (a), or another donor parent, to obtain a second F 1 population,
   (e) allowing the second F 1 population to produce spores while suppressing meiotic recombination,
   (f) producing doubled haploids of the spores of the second F1 population, to obtain a second population of chromosome substitution lines,
   (g) selecting one individual of the first population or the second population to obtain a selected individual,
   (h) crossing the selected individual with a parent of the hybrid plant that corresponds to the first population or the second population from which the selected individual was selected ("the corresponding parent"),
   (i) allowing progeny plant(s) resulting from the crossing of the selected individual and the corresponding parent to produce spores, while allowing meiotic recombination to take place, to obtain a progeny plant(s) population of spores that have received the replacement chromosome or chromosome fragment,
   (j) producing doubled haploids of the spores of the progeny plant(s) population to obtain doubled haploid plant(s) that have received the replacement chromosome or chromosome fragment, and
   (k) crossing the doubled haploid plant(s) with a parent of the hybrid plant that does not correspond to the first population or the second population from which the selected individual ("the non-corresponding parent"), or with another homozygous line, whereby the modified hybrid plant that has acquired a replacement chromosome or chromosome fragment from the donor parent is produced.

2. The method of claim 1, wherein the crossing of step (k) is with the non-corresponding parent.

3. The method of claim 1, wherein the crossing of step (d) is with the donor parent of step (a).

4. The method of claim 3, wherein the crossing of step (k) is with the non-corresponding parent.

5. The method of claim 1, wherein the selecting of step (g) comprises phenotypically analyzing of individuals of the first and second populations.

6. The method of claim 1, wherein the selecting of step (g) comprises genomic testing individuals of the first and second populations.

7. The method of claim 1, wherein the genomic testing comprises DNA marker analysis, single nucleotide polymorphism detection, or DNA-sequencing.

8. The method of claim 5, wherein the crossing of step (d) is with the donor parent of step (a).

9. The method of claim 6, wherein the crossing of step (d) is with the donor parent of step (a).

10. The method of claim 7, wherein the crossing of step (d) is with donor parent.

11. The method of claim 8, wherein the crossing of step (k) is with the non-corresponding parent.

12. The method of claim 9, wherein the crossing of step (k) is with the non-corresponding parent.

13. The method of claim 10, wherein the crossing of step (k) is with the non-corresponding parent.

14. The method of claim 1, wherein in step (b), or step (d), or both steps (b) and (d), suppressing meiotic recombination comprises interfering with a first target gene involved in recombination, and allowing meiotic recombination to take place in step (i) includes an absence of the interfering.

15. The method of claim 14, wherein the interfering comprises destabilizing a target gene mRNA or a target gene transcript, wherein the destabilizing is by a nucleic acid molecule complementary to the target gene mRNA or the target gene transcript, wherein the nucleic acid molecule comprises an antisense RNA, an RNAi molecule, a Virus-Induced Gene Silencing (VIGS) molecule, a co-suppressor molecule, an RNA oligonucleotide or a DNA oligonucleotide.

16. The method of claim 1, wherein allowing recombination to take place in step (i) includes increasing meiotic recombination frequency, wherein increasing meiotic recombination frequency comprises interfering with a second target gene involved in suppression of chromosome interference.

17. The method of claim 16, wherein second the target gene is FANCM.

18. The method of claim 14, wherein allowing meiotic recombination to take place in step (i) includes increasing meiotic recombination frequency comprising interfering with a second target gene involved in suppression of chromosome interference.

19. The method of claim 14, wherein the crossing of step (d) is with the donor parent of step (a) and the crossing of step (k) is with the non-corresponding parent.

20. The method of claim 16, wherein the crossing of step (d) is with the donor parent of step (a), and the crossing of step (k) is with the non-corresponding parent.

* * * * *